United States Patent [19]

Bundy et al.

[11] 3,987,072

[45] Oct. 19, 1976

[54] CIS-4,5-DIDEHYDRO-15- OR 16-ALKYLATED 11-DEOXY-PGE$_1$ ANALOGS

[75] Inventors: Gordon L. Bundy, Kalamazoo; Norman A. Nelson, Galesburg, both of Mich.

[73] Assignee: The Upjohn Company, Kalamazoo, Mich.

[22] Filed: Feb. 10, 1975

[21] Appl. No.: 548,586

[52] U.S. Cl.............................. 260/410; 260/240 R; 260/333; 260/343.2 F; 260/410 S; 260/410.9 R; 260/413; 260/468 D; 260/514 D; 260/598; 260/611 K; 424/305; 424/317
[51] Int. Cl.$^2$........................................ C07C 177/00
[58] Field of Search............ 260/410, 410.9 R, 413, 260/468 D, 514 D

[56] References Cited

FOREIGN PATENTS OR APPLICATIONS 813,547    10/1974    Belgium.............................. 260/468

*Primary Examiner*—Robert Gersil
*Attorney, Agent, or Firm*—Robert A. Armitage

[57] ABSTRACT

This invention relates to a group of cis-4,5-didehydro-11-deoxy-PG$_1$ analogs having variable chain length, optional methyl substitution in the methyl-terminated side-chain, and processes for making them. These compounds are useful for a variety of pharmacological purposes, including ulcer treatment, inhibition of platelet aggregation, increase of nasal patency, and labor induction at term.

7 Claims, No Drawings

CIS-4,5-DIDEHYDRO-15- OR 16-ALKYLATED 11-DEOXY-PGE₁ ANALOGS

BACKGROUND OF THE INVENTION

This invention relates to novel compositions of matter, to novel methods for producing them, and to novel chemical intermediates useful in these processes. Particularly, this invention relates to certain novel analogs of some of the known prostaglandins in which a cis carbon-carbon double bond links C-4 and C-5 in the carboxy-terminated chain and the C-11 hydroxy is replaced with hydrogen.

The known prostaglandins include, for example, prostaglandin E₂ (PGE₂) and prostaglandin F₂ alpha and beta (PGF$_{2\alpha}$ and PGF$_{2\beta}$). Each of the above-mentioned known prostaglandins is a derivative of prostanoic acid which has the following structure and atom numbering:

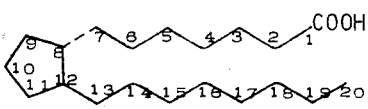

I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE₂ has the following structure:

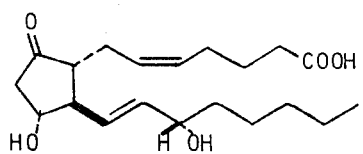

II

PGF$_{2\alpha}$ has the following structure:

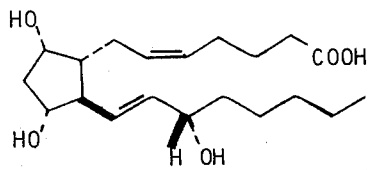

III

PGF$_{2\beta}$ has the following structure:

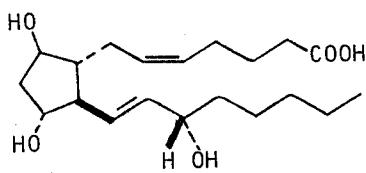

IV

Each of the known PG₁ compounds, PGE₁, PGF$_{1\alpha}$, and PGF$_{1\beta}$, has a structure the same as that shown for the corresponding PG₂ compound except that in each the cis carbon-carbon double bond between C-5 and C-6 is replaced by a single bond. For example, PGE₁ has the following structure:

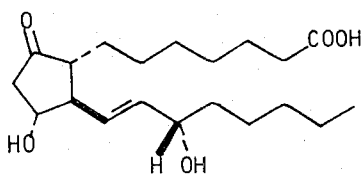

V

In formulas II to V, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Wavy line attachments indicate substituents in either the α or β configuration, or substituents which are α and β isomeric mixtures.

The side-chain hydroxy at C-15 in formulas II to V is in S configuration. See Nature, 212, 38 (1966) for discussion of the stereochemistry of the prostaglandins.

Expressions such as C-15 and the like refer to the carbon atom of the same number in prostanoic acid (See Formula I).

Molecules of the known prostaglandins each have several centers of asymmetry, and can exist in racemic (optically inactive) form and in either of the two enantiomeric (optically active) forms, i.e., the dextrorotatory and levorotatory forms. As drawn, formulas II to V each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to V represents the other enantiomer of that prostaglandin. The racemic form of a prostaglandin contains equal numbers of both enantiomeric molecules, and one of formulas II to V and the mirror image of that formula is needed to represent correctly the corresponding racemic prostaglandin. For convenience hereinafter, use of the terms PGE₁, PGE₂, PGF$_{2\alpha}$, and PGF$_{2\beta}$, will mean the optically active form of that prostaglandin with the same absolute configuration as PGE₁ obtained from mammalian tissues. When reference to the racemic form of one of those prostaglandins is intended, the word "racemic" or "dl" will preceed the prostaglandin name, e.g., racemic PGE₁ or dl-PGF$_{1\alpha}$.

PGE₁, PGE₂, dihydro-PGE₁, PGF$_{1\alpha}$, PGF$_{2\alpha}$, dihydro-PGF$_{3\alpha}$, PGF$_{1\beta}$, PGF$_{2\beta}$, dihydro-PGF$_{1\beta}$, and their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein. A few of those biological responses are systemic blood pressure lowering in the case of the PGE and PGF$_\beta$ compounds as measured, for example, in anesthetized (pentobarbital sodium) pentolinium-treated rats with indwelling aortic and right heart cannulas; stimulation of smooth muscle as shown, for example, by tests on strips on guinea pig ileum, rabbit duodenum, or gerbil colon; potentiation of other smooth muscle stimulants; lipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of these biological response, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds and especially the PGE compounds, are useful in mammals, including man, as nasal decongestants. For this purpose, the compounds are used in a dose range of about 10μg. to about 10 mg. per ml. of a pharmacologically suitable liquid vehicle or as an aerosol spray, both for topical application.

The PGE, PGF$_\alpha$, and PGF$_\beta$ compounds are useful in the treatment of asthma. For example, these compounds are useful as bronchiodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE compound, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGF$_\beta$ compounds are useful as hypotensive agents to reduce blood pressure in mammals, including man. For this purpose, the compounds are administered by intravenous infusion at the rate about 0.01 to about 50 μg. per kg. of body weight per minute or in single or multiple doses of about 25 to 500 μg. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in menstruating female mammals, including humans. By the term menstruating female mammals is meant animals which are mature enough to menstruate but not so old that regular menstruation has ceased. For that purpose the prostaglandin, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second third of the normal mammalian gestation period.

PGE and PGF compounds are useful in causing cervical dilation in pregnant and nonpregnant female mammals for purposes of gynecology and obstetrics. In labor induction and in clinical abortion produced by these compounds, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically.

PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE, PGF$_\alpha$, and PGF$_\beta$ compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally, or alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The PGF$_\alpha$ compounds are useful in the treatment of shock (hemorrhagic shock, endotoxin shock, cardiogenic shock, surgical shock, or toxic shock). Shock is marked by pallor and claminess of the skin, decreased blood pressure, feable and rapid pulse, decreased respiration, restlessness, anxiety, and sometimes unconsciousness. Shock usually follows cases of injury and trauma. Expert and fast emergency measures are required to successfully manage shock conditions. Accordingly, prostaglandins, combined with a pharmaceutical carrier which adapts the prostaglandin for intramuscular, intravenous, or subcutaneous use, are useful, especially in the early stages of shock where increased blood pressure is a critical factor, for aiding and maintaining adequate blood flow, perfusing the vital organs, and exerting a presser response by constricting veins and raising blood pressure to normal levels. Accordingly, the prostaglandins are useful in preventing irreversable shock which is characterized by a profound fall in blood pressure, dilation of veins, and venus blood pooling. In the treatment of shock, the prostaglandin is infused at a dose of 0.1–25 mcg./kg./min. The prostaglandin may advantageously be combined with known vasoconstrictors; such as phenoxybenzamine, norepinephrine, and the like. Further, when used in the treatment of shock the prostaglandin combined with steroids (such as, hydrocortisone or methylprednisolone), tranquilizers, and antibiotics (such as, lincomycin or clindamycin).

The PGE, PGF$_\alpha$, and PGF$_\beta$ compounds are useful in domestic animals as an abortifacient (especially for feedlot heifers), as an aid to estrus detection, and for regulation or synchronization of estrus. Domestic animals include horses, cattle, sheep, and swine.

The regulation or synchronization of estrus, as well as estrus detection, allows for more efficient management of both conception and labor by enabling a herdsman to breed all his female animals in short predefined interval. This resuls in a higher percentage of live births than the percentage achieved by natural control. The PG is injected or applied in a feed at doses of 0.1–100 mg. per animal per day and may be combined with other agents such as steroids. Dosing schedules will depend on the species treated. For example, mares are given prostaglandins 5–8 days after ovulation and return to estrus. Cattle, are treated at regular intervals over a 3 week period to advantageously bring all into estrus at the same time.

SUMMARY OF THE INVENTION

This invention provides novel 4,5-didehydro-11-deoxy-PG analogs. This invention further provides esters and pharmacologically acceptable salts of these analogs. This invention further provides novel processes for preparing these analogs and their esters and salts. The present invention comprises:

a compound of the formula

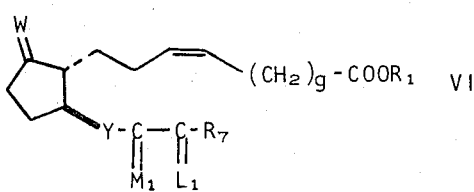

or a mixture comprising that compound and the enantiomer thereof wherein W is

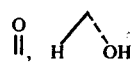

or

wherein $g$ is 2 to 4, inclusive;
wherein L$_1$ is

or a mixture of

and

wherein R$_3$ and R$_4$ are hydrogen or methyl, being the same or different, wherein M$_1$ is

or

wherein R$_5$ and R$_6$ are hydrogen or methyl, with the proviso that R$_5$ is methyl only when R$_6$ is hydrogen and R$_6$ is methyl only when R$_5$ is hydrogen;
wherein R$_1$ is hydrogen, alkyl or one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation;
wherein R$_7$ is —(CH$_2$)$_m$—CH$_3$, wherein m is one to 5, inclusive; and
wherein Y is —CH$_2$CH$_2$— or trans-CH=CH—.

The novel prostaglandin-type compounds of this invention include the separate C-15 epimers wherein M$_1$ is either

or

i.e., wherein —OR$_6$ is in either the natural (alpha or L) or epi (beta or D) configuration. The terms D and L relate to the absolute configuration of D- or L-glyceraldehyde using the standard Fischer convention. See M. Hamberg, Advan. Bio. Sci. 9, 847 (1963).

The novel 4,5-didehydro-11-deoxy compounds of this invention are named as PGE$_1$-type compounds when W is

PGF$_{1\alpha}$ -type compounds when W is

and PGF$_{1\beta}$ -type compounds when W is

Further, when Y is —CH$_2$CH$_2$— the novel PG-type compounds of this invention are further named as "13,14-dihydro" compounds.

Further included within the scope of the novel compounds of this invention are the carboxy side chain homologs and the methyl terminated side-chain homologs and nor compounds. Accordingly, those PG-type compounds of this invention wherein there are 8 or 9 carbon atoms in the carboxy terminated side-chain instead of 7 carbon atoms as in PGE$_1$ obtained from mammalian tissues, are named "2a-homo" or "2a,2b-dihomo" compounds, respectively. The additional carbon atoms are designated as "2a" and "2b," and are named as being inserted between C-2 and C-3. Further, those compounds wherein the methyl-terminated side chain contain one or 2 additional carbon atoms, as compared to PGE$_1$ as obtained from mammalian tissues, are named as "20-methyl" or "20-ethyl" compounds, respectively. Also, those PG-type compounds of this invention wherein the methyl terminated side chain contains one or 2 fewer carbon atoms and PGE$_1$ is obtained from mammalian tissues are named as "20-nor" or "19,20-dinor" compounds respectively.

Also included in the novel PG-type compounds of this invention are those compounds wherein the C-16 hydrogens are replaced by one or two methyl groups. Accordingly, these compounds are named "16-methyl" and "16,16-dimethyl," respectively.

Further, "15-methyl" or "15-methyl ether" PG-type compounds are provided by this invention when R$_5$ or R$_6$ is methyl, respectively. Further, both epimeric configurations at C-15 are provided. Accordingly, when M$_1$ is

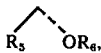

the PG-type compounds of this invention possess the same absolute configuration at C-15 as PGE$_1$ obtained from mammalian tissues. When M$_1$ is

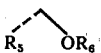

the compounds described are the 15-epimers, and are named as "15-epi" compounds.

The above formulas plus the respective mirror images of these formulas describe mixtures of an enantiomer within the scope of this invention. For convenience racemic mixtures, containing equal amounts of each enantiomer are proceeded by the prefix "racemic" ("rac." or "dl") before the compound. When the prefix is absent, the single enantiomer represented by one of the above formulas is designated. Examples of alkyl of 1 to 12 carbon atoms, inclusive, are methyl, ethyl, propyl, butyl, pentyl, hexyl, heptyl, octyl, nonyl, decyl, undecyl, dodecyl, and the isomeric forms thereof. Examples of cycloalkyl of 3 to 10 carbon atoms, inclusive, which includes alkyl substituted, cycloalkyl are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-terbutylcyclohexyl, 3-isopropylcyclohexyl, 2,2-dimethylcyclohexyl, cycloheptyl, cycloheptyloctyl, cyclononyl, and cyclodecyl. Examples of aralkyl of 7 to 12 carbon atoms, inclusive, are benzyl, phenethyl, 1-phenethyl, 2-phenpropyl, 4-phenbutyl, 3-phenbutyl, 2-(1-naphthylethyl), and 1-(2-naphthylmethyl). Examples of phenyl substituted with 1, 2, or 3 chloro or alkyl of 1 to 4 carbon atoms, inclusive, are p-chlorophenyl, m-chlorophenyl, o-chlorophenyl, 2,4-difluorophenyl, 2,4,6-trichlorophenyl, m-tolyl, p-tolyl, o-tolyl, p-phenethyl, p-tertbutylphenyl, 2,5-dimethylphenyl, 4-chloro-2-methylphenyl, 2,4-dichloro-3-methylphenyl.

The novel PG analogs of this invention correspond to the prostaglandins described above, in that the novel PG analogs exhibit prostaglandin-like activity. Specifically, the 11-deoxy-PGE-type compounds of this invention correspond to the PGE compounds described above, in that these novel PGE-type compounds are useful for each of the above described purposes for which the PGE compounds are used, and are used in the same manner as the PGE compounds, as described above. Further, the 11-deoxy-PGF$_\alpha$ -type compounds of this invention correspond to the PGF$_\alpha$ compounds described above, in that these novel PGF$_\alpha$ -type compounds are useful for each of the above-described purposes for which the PGF$_\alpha$ compounds are used, and are used in the same manner as the PGF$_\alpha$ compounds, as described above. Finally, the 11-deoxy-PGF$_\beta$ -type compounds of this invention correspond to the PGF$_\beta$ compounds described above, in that these novel PGF$_\beta$ -type compounds are useful for each of the above-described purposes for which the PGF$_\beta$ compounds are used, and are used in the same manner as the PGF$_\beta$ compounds, as described above.

The prostaglandins described above are all potent in causing multiple biological responses even at low doses. Moreover, for many applications these prostaglandins have an inconveniently short duration of biological activity. In striking contrast, the novel prostaglandin analogs of this invention are substantially more specific with regard to potency in causing prostaglandin-type responses, and have a substantially longer duration of biological activity.

Accordingly, each of the novel prostaglandin analogs of this invention is surprisingly and unexpectedly more useful than one of the corresponding prostaglandins, described above, for at least one of the pharmacological purposes indicated for the corresponding prostaglandin, because each of the novel prostaglandin analogs has a different and narrower spectrum of biological potency than the corresponding prostaglandin, and therefore is more specific in its activity and causes smaller and fewer undesired side effects than when the corresponding prostaglandin is used for the same purpose. Moreover, because of its prolonged activity, fewer and smaller doses of the novel prostaglandin analog are frequently used to obtain the desired result.

Another advantage of the novel compounds of this invention, especially the preferred compounds defined hereinbelow, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

As discussed above, the novel compounds of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

Another advantage of the novel compounds of this invention is that their unique chemical structure renders them less sensitive to dehydration and rearrangement. Accordingly, these compounds exhibit a surprising and unexpected duration of shelf life.

The novel PG analogs of this invention are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel PG analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)-aminomethane, N-phenylethanolamine, N-(p-tert-amylphenyl)-diethanolamine, galactamine, N-methylgycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of this invention are preferred.

Those compounds wherein g is 2 or 4 are preferred. Those compounds wherein g is 2 are especially preferred. Those compounds wherein $R_5$ and $R_6$ are both hydrogen are preferred when at least one of $R_3$ and $R_4$ is methyl. Those compounds in which $R_3$ and $R_4$ are both hydrogen are preferred when one of $R_5$ and $R_6$ is methyl. Those compounds are preferred wherein at least one of $R_3$, $R_4$, $R_5$, and $R_6$ is methyl. It is preferred that m be 3.

Reference to Chart A will make clear the process by which the formula X aldehyde is transformed into the novel PG-type compounds of this invention. The aldehyde of formula X is known in the art See Crabbe, et al., Tetrahedron Letters No. 2, 115 (1972) for racemic form. Employed herein are methods known in the art. See E. J. Corey et al., Journal of the American Chemical Society, 91, 5675 (1969).

Chart A

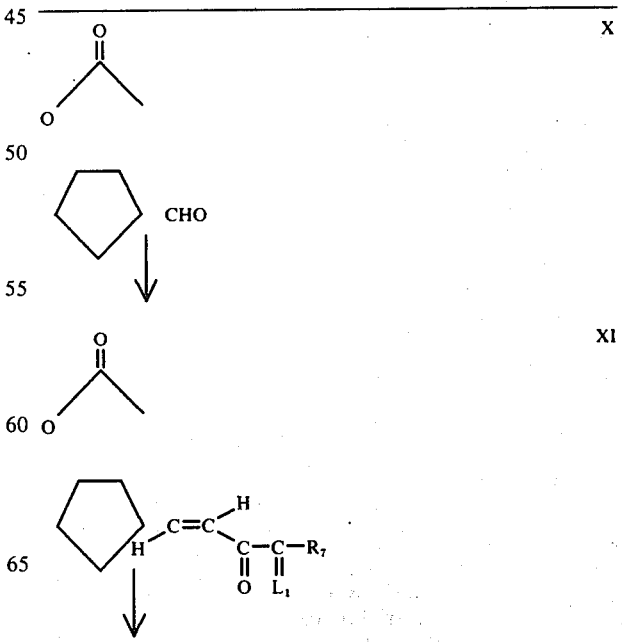

-continued
Chart A
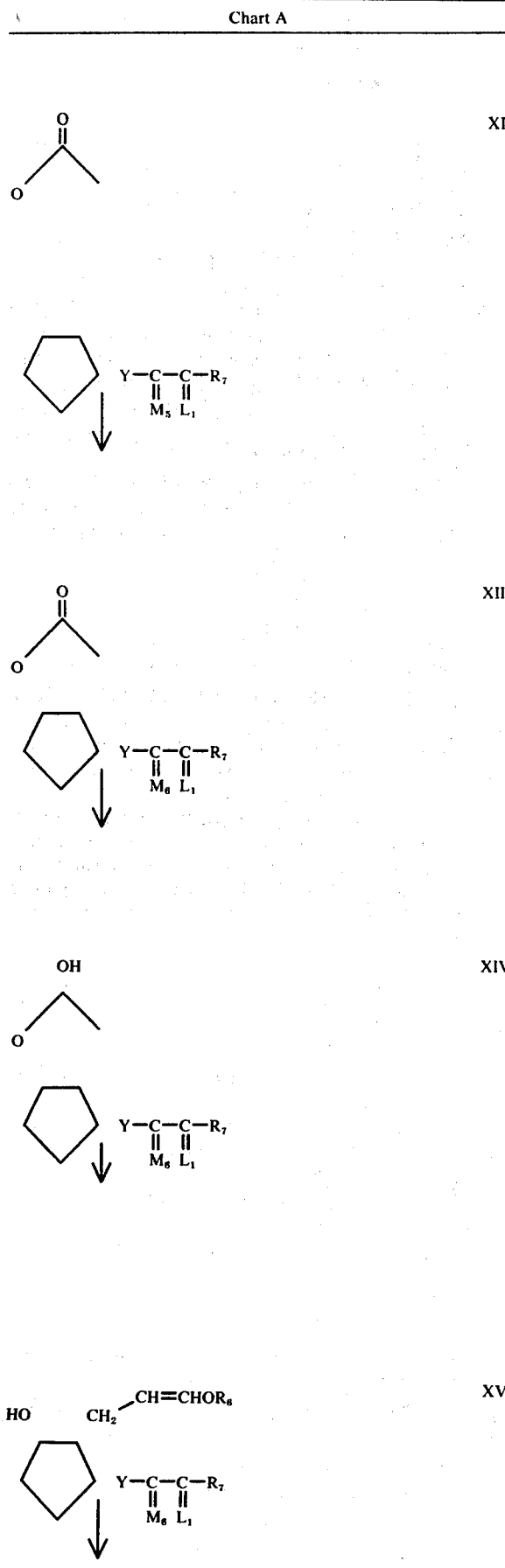
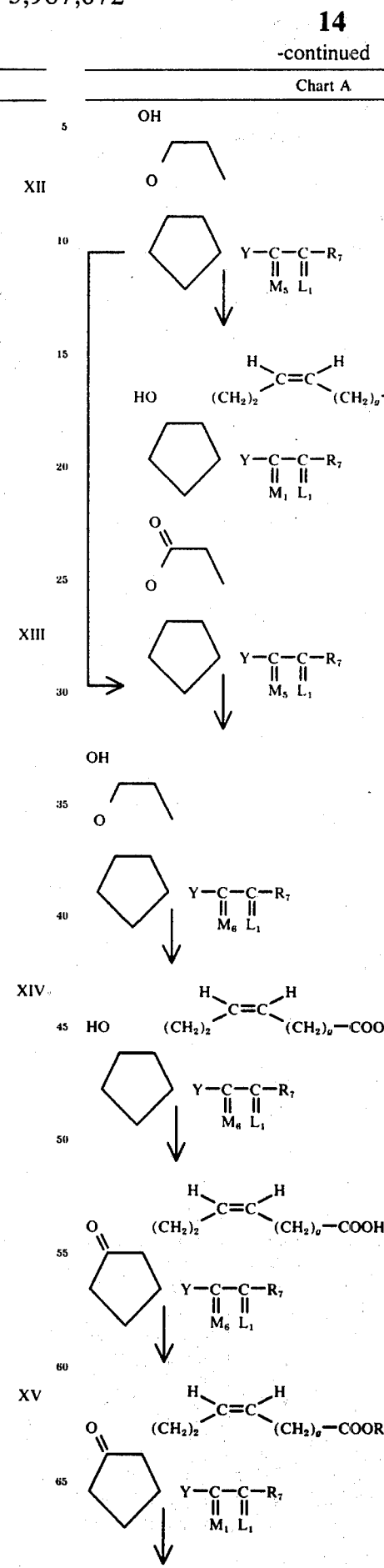

-continued

Chart A

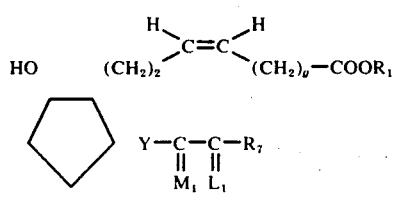

XXIII

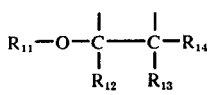

With respect to Chart A. $L_1$, $M_1$, $R_1$, $g$, and $R_7$ are as defined above and $M_5$ is

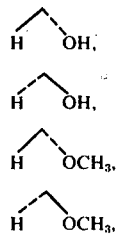

or a mixture of

and

;

$M_6$ is

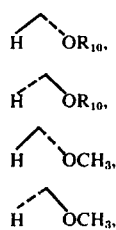

or a mixture of

and

, wherein $R_{10}$ is a "blocking group" which is defined as any group which replaces hydrogen of the hydroxyl groups, which is not attacked by nor is reactive to the reagents used in the respective transformations to reagents used in the respective transformations to the extent that the hydroxyl group is, and which is subsequently replaceable by hydrogen at a later stage in the preparation of the prostaglandinlike products. Several blocking groups are known in the art, e.g. tetrahydropyranyl and substituted tetrahydropyranyl (see Corey, Proceedings of the Robert A. Welch Foundation Conferences on Chemical Research XII, Organic Synthesis, pp. 51–79 (1969)). Those blocking groups which have been found useful include (a) tetrahydropyranyl; (b) tetrahydrofuranyl; or (c) a group of the formula $$R_{11}-O-\underset{\underset{R_{12}}{|}}{\overset{|}{C}}-\underset{\underset{R_{13}}{|}}{\overset{|}{C}}-R_{14}$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{12}$ and $R_{13}$ are the same or different, being hydrogen, alkyl of one to 4 carbon atoms, inclusive, phenyl, or phenyl substituted with one, 2, or 3 alkyl of one to 4 carbon atoms, inclusive, or, when $R_{12}$ and $R_{13}$ are taken together, $-(CH_2)_b-$ or $-(CH_2)_c-O-(CH_2)_d-$ wherein $b$ is 3, 4, or 5, $c$ is one, 2, or 3, and $d$ is one, 2, or 3 with the proviso that $c$ plus $d$ is 2, 3, or 4, and wherein $R_{14}$ is hydrogen or phenyl.

The formula XI compound is obtained by Wittig alkylation of the formula X compound using the sodio derivative of an appropriate 2-oxo-phosphonate having the formula

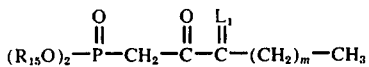

wherein $m$ and $L_1$ are as defined above, and wherein $R_{15}$ is alkyl of one to 8 carbon atoms, especially methyl. The trans enone lactone (formula XI) is obtained stereospecifically. See D. H. Wadsworth, et al., J. Org. Chem. Vol. 30, p. 680 (1965).

The phosphonates are prepared and used by methods known in the art. See Wadsworth et al., reference cited above. Conveniently, the appropriate aliphatic acid ester is condensed with dimethyl methylphosphonate in the presence of n-butyllithium. For this purpose, acids of the general formula

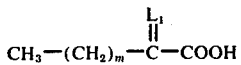

wherein $m$ and $L_1$ are as defined above, are used in the form of lower alkyl esters, preferably methyl or ethyl. For this purpose methyl esters are readily formed from the acid by reaction with diazomethane. These alkyl-substituted alkanoic acids are known in the art or can be prepared by methods known in the art.

Alternatively, there can be employed in the reaction, certain phosphoranes of the formula

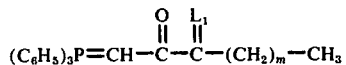

These phosphoranes are prepared and used by methods known in the art. Conveniently, the appropriate ketone compound of the formula

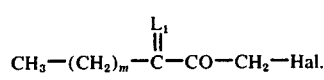

wherein Hal is chloro, bromo, or iodo, is condensed with triphenylphosphine and the condensation product is treated with alkali to produce the desired phosphorane compound. The halo-ketone starting compound is prepared in a known way.

The formula XII compound wherein $M_5$ is

or

is obtained as a mixture of alpha and beta hydroxy isomers by non-ethylenic reduction of the formula XI compound, followed by hydrogenation at the C-13 to C-14 bond when Y is —$CH_2CH_2$— in formula XII. Hydrogenation is accomplished by known methods in the art, e.g. use of metal catalysts. For the reduction, use is made of any of the known ketonic carbonyl reducing agents which do not reduce ester or acid groups or carbon-carbon double bonds when Y is trans-CH=CH— in formula XII. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, and when carbon-carbon double bond reduction is not a problem, the boranes, e.g., disiamylborane (bis-3-methyl-2-butylborane).

For production of natural-configuration prostaglandins, the alpha form of the above compound is separated from the beta isomer by silica gel chromatography using methods known in the art, separation of the epimers may alternatively be performed on the final PG-type products.

The formula XII compound wherein $M_5$ is

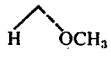

or

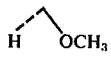

is obtained by nonethylenic reduction, hydrogenation of the formula XI compound, and separation of the C-15 epimers, as described above, followed by alkylation of the side-chain hydroxy of this compound, thereby replacing the hydroxy with the —$OCH_3$ moiety. For this purpose, diazomethane may be employed, preferably in the presence of a Lewis acid, e.g. boron trifluoride etherate, aluminum chloride, or fluoboric acid. See Fieser et al., "Reagents for Organic Synthesis," John Wiley and Sons, Inc., N.Y. (1967), p. 191. The reaction is carried out by mixing a solution of the diazolalkane in a suitable inert solvent, preferably ethyl ether, with the 15-hydroxy compound. Generally the reaction proceeds at about 25° C.

Another method for the alkylation of the side chain hydroxy is by reaction with an alcohol in the presence of boron trifluoride etherate yield the methyl ether. The reaction is done at about 25° C. and is conveniently followed with thin layer chromatography (TLC). This method however often results in C-15 epimerization.

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

The formula XII compound wherein $M_5$ is a mixture of

and

is obtained by replacing the side-chain oxo with $M_5$ by a conventional Grignard reaction, employing $CH_3MgHal$, wherein Hal is chloro, bromo, or iodo. Alternatively, the alkylation proceeds by reaction of the formula XI compound as known in the art with trimethylaluminum. For the production of the 15,16,16-trimethyl compounds of this invention, the use of trimethylaluminum is preferred.

The 15-methyl compounds of this invention are conveniently separated from their respective 15-epimers as prostaglandin-type methyl esters.

The formula XIII lactone is obtained by replacing the hydrogen atom of any hydroxy group of the $M_5$ moiety in formula XII with a blocking group. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in large excess, preferably 1.2 to 20 times theory. The reaction is carried out at about 20°–50° C.

When the blocking group is of the formula

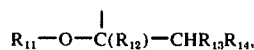

as defined above, the appropriate reagent is a vinyl ether, e.g. isobutyl vinyl ether or any vinyl ether of the formula

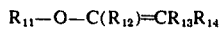

wherein $R_{11}$, $R_{12}$, $R_{13}$, and $R_{14}$ are as defined above; or an unsaturated cyclic or heterocyclic compound, e.g. 1-cyclohexen-1-yl methyl ether

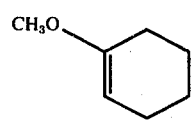

or 5,6-dihydro-4-methoxy-2H-pyran

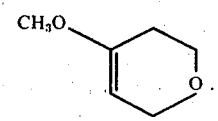

See C. B. Reese et al., J. Am. Chem. Soc. 89, 3366 (1967). The reaction conditions for such vinyl ethers and unsaturates are similar to those for dihydropyran above.

The formula XIV lactol is obtained on reduction of lactone XIII without reducing the ethylenic group. For this purpose, diisobutylaluminum hydride is used as known in the art. The reduction is preferably done at −60° to −70° C.

The formula XIV compound then undergoes condensation to form the formula-XV enol ethers. For this purpose, a hydrocarbyloxymethylenetriphenylphosphorane is useful, e.g. $(C_6H_5)_3P\!\!=\!\!CHOR_8$ wherein $R_8$ is hydrocarbyl. The reagent is conveniently prepared from a corresponding quaternary phosphonium halide and a base, e.g. butyllithium or phenyllithium, at a low temperature, e.g. preferably below −10° C. The formula XIV lactol is mixed with the reagent and the condensation proceeds smoothly within the temperature range −30° C. to +30° C. At higher temperatures the reagent is unstable, whereas at low temperatures the rate of condensation is undesirably slow. Examples of the alkoxymethylenetriphenylphosphoranes preferred for forming the formula XV enol ethers are methoxy-, ethoxy-, propoxy-, isopropoxy-, butoxy-, isobutoxy-, sec-butoxy-, and tert-butoxymethylenetriphenylphosphorane.

Various hydrocarbyloxymethylenetriphenylphosphoranes which may be substituted for the alkoxymethylenetriphenylphosphoranes and are therefore useful for preparing formula XXXVII intermediates wherein $R_8$ is hydrocarbyl, include alkoxy (of 1 to 4 carbon atoms), aralkoxy-, cycloalkoxy-, and aryloxymethylenetriphenylphosphoranes. Examples of these hydrocarbyloxymethylenetriphenylphosphoranes are 2-methylbutyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenyl propyloxy-, cyclohexyloxy-, phenoxy-, and p-methylphenoxymethylenetriphenylphosphorane. See, for example, Organic Reactions, Vol. 14, pages 346–348, John Wiley and Sons, Inc., N.Y., (1965).

The formula XV enol ether intermediates are then hydrolyzed to the formula XVI lactols. This hydrolysis is done under acidic conditions, for example with perchloric acid or acetic acid. Tetrahydrofuran is a suitable diluent for this reaction mixture. Reaction temperatures of from 10° C. to 100° C. are employed. The length of time required for hydrolysis is determined in part by the hydrolysis temperature. With acetic acid-water-tetrahydrofuran at about 60° C., several hours are sufficient.

Finally, the formula XVI lactols are transformed to the formula-XVII PGF-type products by condensation with a Wittig reagent derived from ω-carboxyalkyltriphenylphosphonium halide and sodio methyl-sulfinylcarbanide, followed by methyl esterification when $R_5$ is methyl, by the procedure described below, separation of the C-15 epimers, for example, by silica gel chromatography, when $R_5$ is methyl, and transformation of the carboxy hydrogen or carboxy methyl ester to the $R_1$ moiety, by the procedures described hereinbelow.

Alternatively, in the preparation of the PGE-type compounds of this invention the formula XVI compound is transformed into the formula XVIII lactone. This transformation is carried out using, for example, silver oxide as an oxidizing reagent, followed by treatment with for example, dihydropyran and pyridine hydrochloride.

The formula XVIII lactone may then be converted to the formula XIX lactol-ether by the procedure described for the reduction and etherification of the formula XII compound in the preparation of the formula XIV compound.

Thereafter, the formula XX compound is prepared from the formula XIX compound by a Wittig alkylation using the Wittig reagent described in the preation of the formula XVII compound. The formula XXI compound is then prepared from the formula XX compound by oxidation. Oxidation reagents useful for this transformation are known in the art. An especially useful reagent for this purpose is the Collins reagent i.e. chromium trioxide in pyridine. See J. C. Collins et al., Tetrahedron Letters 3363 (1968). Dichloromethane is a suitable diluent for this purpose. A slight excess of oxidant is used. Reaction temperatures below 20° C. should be used. Preferred reaction temperatures are −10° to +10° C. The oxidation proceeds rapidly and usually is complete in about 5 to 20 min. The formula XXII compound is then prepared from the formula XXI compound by hydrolysis of the blocking group under acidic conditions, as is known in the art, followed by methyl esterification and separation of the C-15 epimers when such separation has not heretofore been achieved, followed by transformation of the carboxy hydrogen or carboxy methyl ester to the $R_1$ moiety, according to procedures hereinbelow described.

The formula XXIII compound is then prepared from the formula XXII compound by a ring carbonyl reduction, followed by separation of the 9β-hydroxy epimer.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium (tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom, et al., cited above, Granstrom et al., J. Biol. Chem. 240, 457 (1965), and Green et al., J. Lipid Research 5, 117 (1964). Separation methods known to be useful are partition chromatographic procedures, both normal and reversed phase, preparative thin layer chromatography, and countercurrent distribution procedures.

Accordingly, formulas XVII, XXI, and XXIII provide the novel 4,5-didehydro-11-deoxy-PGF$_α$, PGE, and PGF$_β$ -type compounds of this invention.

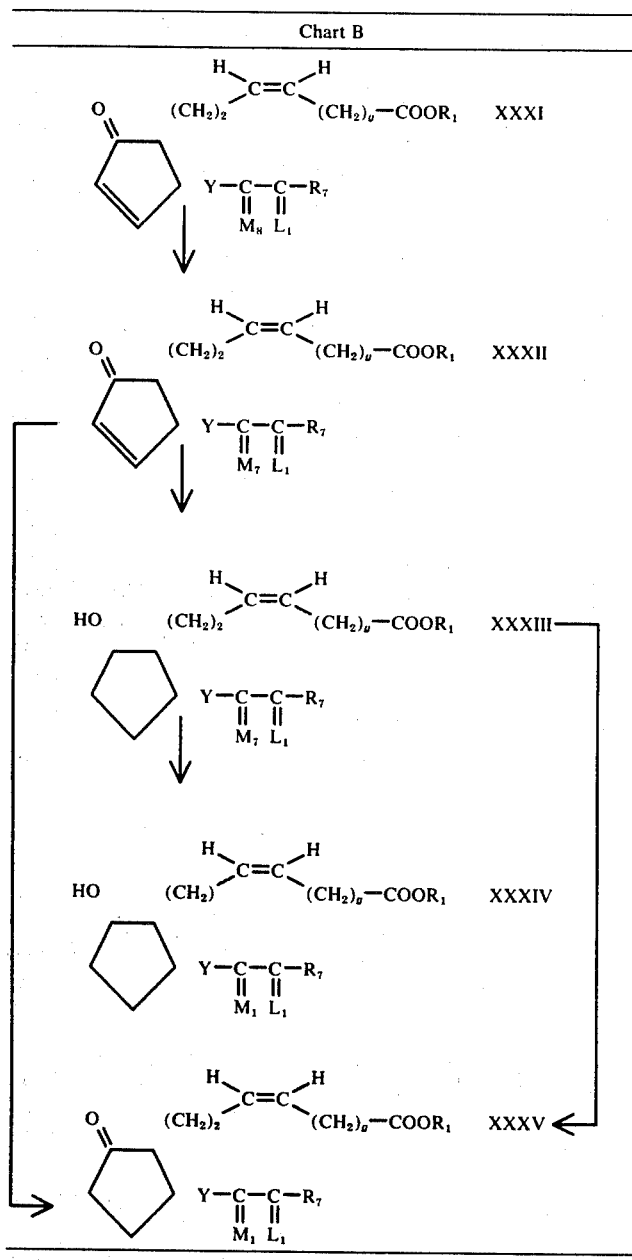

Chart B provides a method whereby the novel PG-type compounds of this invention are prepared from corresponding PGA-type compounds. With respect to Chart B, $R_1$, $R_7$, Y, g, and $L_1$ are as defined above. $M_8$ is

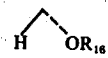

or

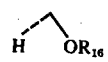

wherein $R_{16}$ is hydrogen, alkanoyl of 2 to 8 carbon atoms, inclusive, tetrahydropyranyl, tetrahydrofuranyl, or a group of the formula

wherein $R_{11}$, $R_{12}$, $R_{13}$, and $R_{14}$ are as defined above. $M_7$ is

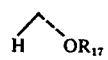

or

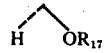

wherein $R_{17}$ is a blocking group. This blocking group functions to prevent attack on the hdroxyl group by subsequent reagents, especially the oxidizing reagent for transforming

or

at C-9 to oxo. It is a further requirement of this blocking group that it be replaceable by hydrogen at a later stage in the preparation of the prostaglandin-like products. Blocking groups which have been found useful include alkanoyl, tetrahydropyranyl, tetrahydrofuranyl, a group of the formula

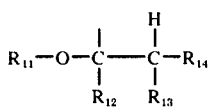

as defined above, and silyl of the formula $-Si(G)_3$ wherein G is alkyl of one to 4 carbon atoms, inclusive, phenyl, phenyl substituted with onne or 2 fluoro, chloro, or alkyl of one to 4 carbon atoms, inclusive, or aralkyl of 7 to 12 carbon atoms, inclusive.

In replacing the hydrogen of the hydroxyl group with an alkanoyl blocking group, methods known in the art are used. Thus, for example, acetic anhydride or acetyl chloride is reacted with the formula XXXI compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene, or chloroform. The acylating agent is used either in stoichiometric amount or in excess. If the acyl chloride is not available, it is made from the corresponding acid and phosphorus pentachloride or thionyl chloride as is known in the art.

When the blocking group is silyl of the formula $-Si(G)_3$, the formula XXXI compound is transformed to a silyl derivative of formula XXXII by procedures known in the art. See, for example, Pierce, "Silylation of Organic Compounds," Pierce Chemical Co., Rockford, Ill. (1968). The necessary silylating agents for these transformations are known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotrimethylsilane, chlorotiisobutylsilane, chlorotriphenylsilane, and tribenzylchlorosilane. Alternatively the chlorosilane is used with the corresponding disilazanes. Examples of other silylating agents suitable for forming the formula XXXII intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

When the blocking group is tetrahydropyranyl or tetrahydrofuranyl, the appropriate reagent, e.g. 2,3-dihypyran or 2,3-dihydrofuran, is used in an inert solvent such as dichloromethane, in the presence of an acid condensing agent such as p-toluenesulfonic acid or pyridine hydrochloride. The reagent is used in excess, preferably 4 to 10 times theory. The reaction is carried out at about 20°–50° C.

When the blocking group is of the formula

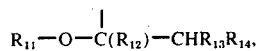

as defined above, the appropriate reagent is a vinyl ether, e.g. isobutyl vinyl ether or any vinyl ether of the formula

wherein $R_{11}$, $R_{12}$, $R_{13}$, and $R_{14}$ are as defined above; or an unsaturated cyclic or heterocyclic compound, e.g. 1-cyclohexen-1-yl methyl ether

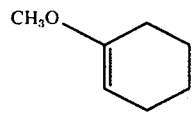

or 5,6-dihydro-4-methoxy-2H-pyran

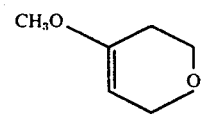

See C. B. Reese et al., J. Am. Chem. Soc, 89, 3366 (1967). The reaction conditions for such vinyl ethers and unsaturates are similar to those for dihydropyran above.

The formula XXXI 4,5-didehydro-PGA$_1$-type compound is prepared by methods known in the art. For example, the PGA$_1$-type compound may be prepared from the corresponding PGE-type compound by dehydration, as is known in the art. The various PGE-type compounds corresponding to the formula XXXI PGA-type compounds are known in the art or may be prepared by methods known in the art.

As described hereinabove the formula XXXII compound is prepared from the formula XXXI compound by replacing any hydroxy group with a blocking group as described above. The formula XXXIII compound is then prepared from the formula XXXII compound by a ring carbonyl reduction, using for example an alkaline metal borohydride. For this purpose sodium, potassium, or lithium borohydride is effectively used in aqueous solution. Reaction temperatures of about −20° C. are employed in the reaction.

The formula XXXIV compound is then prepared from the formula XXXIII compound by hydrolysis of the blocking group, followed by separation of the C-9 epimers using, for example, silica gel chromatography. Silyl blocking groups, for example, are readily removed by prior art procedures described in Pierce, cited above, especially page 447 thereof. The formula XXXV compound may be prepared from either the formula XXXIII compound or the formula XXXII compound. When the formula XXXV compound is prepared from the formula XXXII compound procedures described above for the transformation of PGF-type compounds to PGE-type compounds are employed, followed by hydrolysis of the blocking groups, as described above.

When the formula XXXV compound is prepared from the formula XXXII compound, selective hydrogenation of ring unsaturation, followed by hydrolysis of the blocking groups, is employed. For hydrogenation, a hydrogen atmosphere of about 3.5 kg./cm.² is employed over a 5 to 10 percent palladium or rhodium catalyst on carbon alumina or other suitable support. Suitable organic diluents are employed, e.g. ethyl acetate, methanol, ethanol, or diethyl ether. The reaction proceeds at temperatures between −30° and +50° C.

Accordingly, in Chart B there are prepared PGE, PGF$_\alpha$, and PGF$_\beta$ -type compounds of this invention.

With respect to Chart C, $R_1$, $R_7$, g, $M_{12}$, and $L_1$ are as defined herein. $M_9$ is

or

$M_{10}$ is

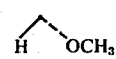

or

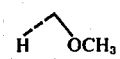

$M_{11}$ is a mixture of

and

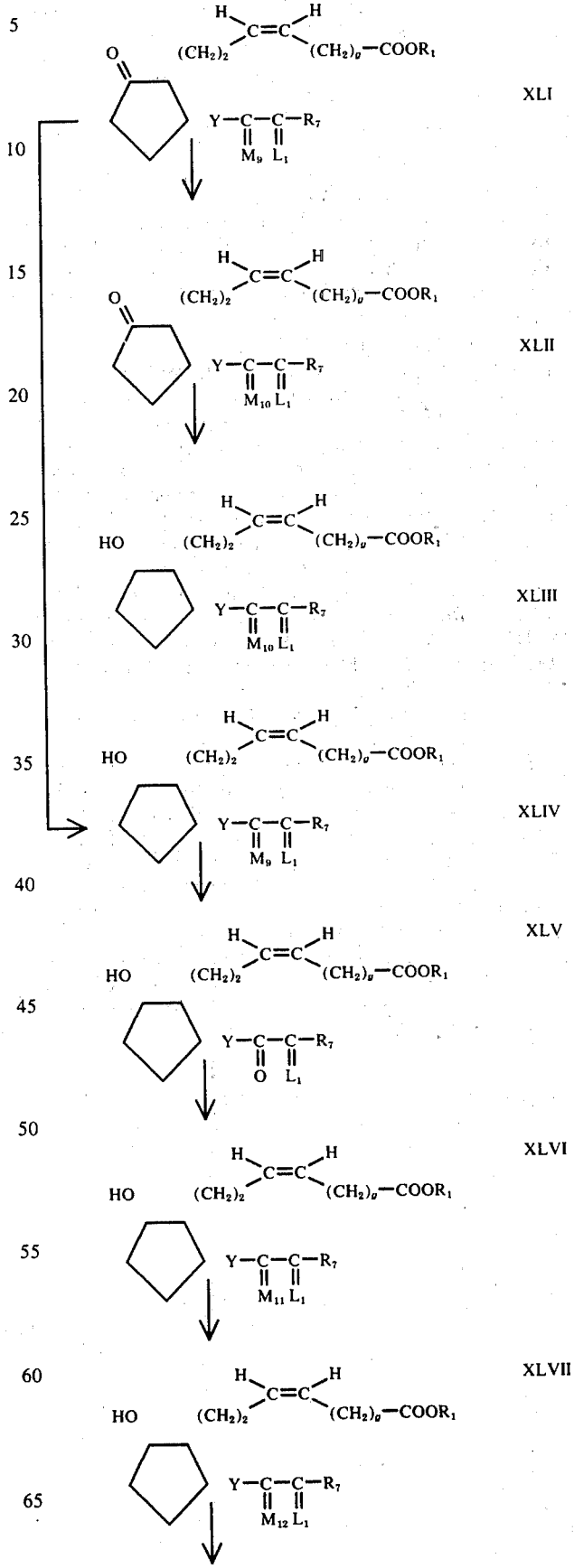

Chart C

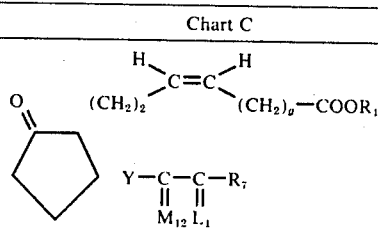
XLVIII

The formula XLII compound is prepared from the formula XLI compound by a methyl-etherification at the C-15 position. This esterification is advantageously accomplished by reaction of the formula XLI compound with methyl idodide in the presence of silver oxide, at reflux in benzene. The formula XLIII compound may then be prepared for the formula XLII compound by a ring carbonyl reduction, as described above.

The formula XLIV compound is prepared from the formula XLI compound by a ring carbonyl reduction. Reduction methods as described above are employed. The formula XLV compound is then prepared from the formula XLIV compound by oxidation with reagents such as 2,3-dichloro, 5,6-dicyano, 1,4-benzoquinone, activated manganese dioxide, or nickel peroxide (see Fieser et al., Reagents for Organic Synthesis, John Wiley and Sons, Inc., N.Y., pg. 215, 637, and 731).

The formula XLVI compound is then prepared from the formula XLV compound by a Grignard reaction, or reacting the formula XLV compound with trimethylaluminum, as described above for the preparation of the 15-methyl compounds of this invention.

The formula XLVII compound is then prepared from the formula XLVI compound by separation of the C-15 epimers. Advantageously, separation is effected on PG-type methyl esters ($R_1$ is methyl). The formula XLVIII is then prepared from the formula XLVII compound by oxidation of the C-9 hydroxy to a C-9 oxo, as described above for the preparation of the PGE-type compounds from the PGF-type compounds.

Chart D provides a preferred process whereby the 15-alkyl-13,14-dihydro-PG-type compounds of this invention are prepared. $R_7$, g, and $L_1$ are as defined above. $M_{11}$ is a mixture of

and

$M_{12}$ is

or

$M_{14}$ is a mixture of

and

wherein $R_{22}$ is benzoyl. $M_{15}$ is

or

, wherein $R_{22}$ is benzoyl.

Chart D

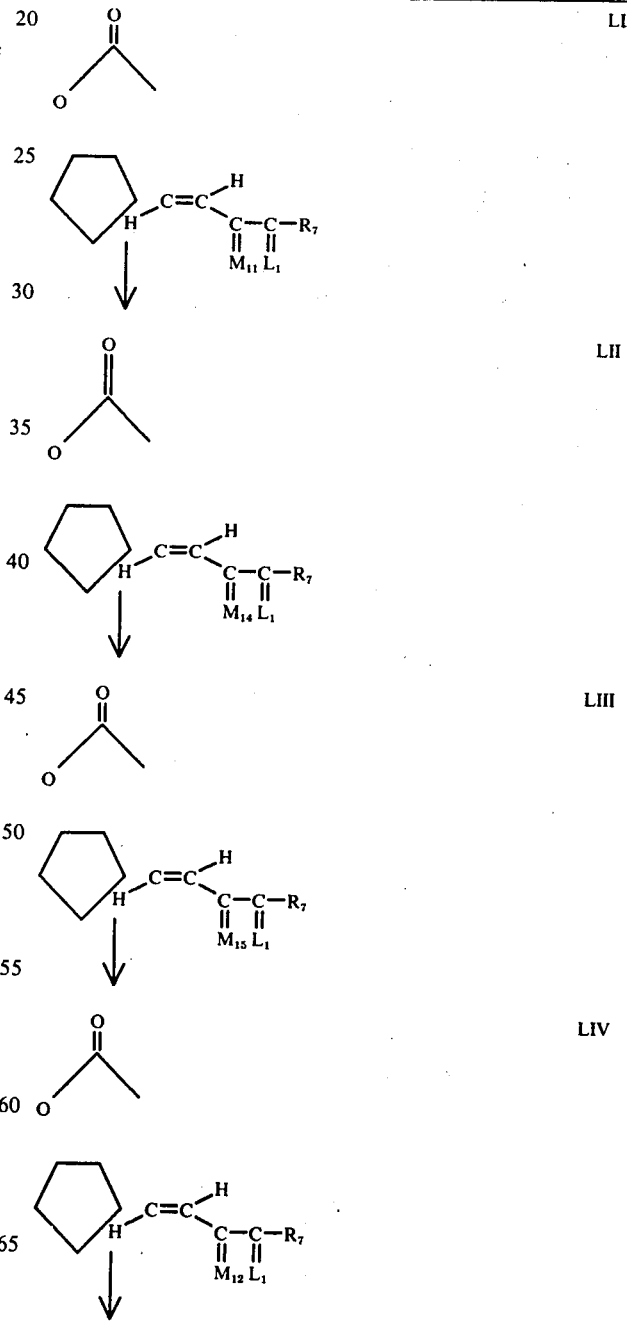

-continued

Chart D

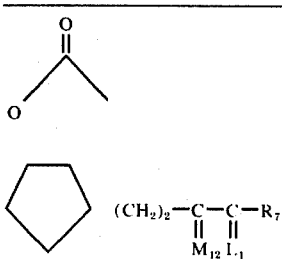

LV

The formula LII compound is prepared from the formula LI compound by benzoylation. Benzoylation is accomplished, for example, by reaction of the formula LI compound with benzoyl chloride. The reaction proceeds at 0° C. to completion in about 15 min. The formula LIII compound is prepared from the formula LII compound by silica gel chromatographic separation.

The formula LIV compound is then prepared from the formula LIII compound by hydrolysis of the benzoyl group. Hydrolysis may be accomplished by treatment of the formula LIII compound with an alkaline metal methoxide in methanol, quenched by the addition of sodium bisulfate.

The formula LV compound may then be prepared from the formula LIV compound by catalytic hydrogenation. Methods described hereinabove, i.e. the use of metal catalysts, are employed. Finally the formula LV lactone is transformed into corresponding PG-type compounds following the procedure of Chart A.

In all of the above-described reactions, the products are separated by conventional means from the starting materials and impurities, for example by silica gel chromatography monitored by thin-layer chromatography (TLC).

Optically active compounds are obtained from optically active intermediates according to the process steps of the above charts. When racemic intermediates are used in reactions corresponding to the processes of the above charts, and racemic products are obtained, these racemic products may be used in their racemic form or, if preferred, they may be resolved as optically active isomers by procedures known in the art.

For example, when final PG-type compounds are free acids the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula VI is then obtained by treatment of the salt with an acid by known general procedures.

Referring to Chart A, when a formula XI compound is prepared by reacting a racemic compound corresponding to formula X with a racemic Wittig reagent, there are obtained two pairs of racemates which are separable into pairs of racemic compounds by methods known in the art, e.g. silica gel chromatography. When a racemic compound corresponding to formula X is reacted with an optically active isomer of the Wittig reagent, there are obtained two diastereomers corresponding to the formula XI compound which are separated by conventional methods, e.g. by silica gel chromatography.

It is preferred that the formula X compound be used in the optically active form which will lead to an 11-deoxy prostaglandin analog of the natural configuration. For this purpose, there is provided a process for resolving a racemic mixture of an oxo compound of the formula

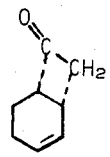

LX or

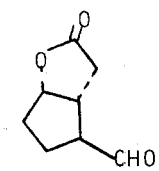

X and of the mirror image thereof, which comprises the steps of
  a. converting the oxo compound by reaction with an optically active ephedrine to a mixture of oxazolidine diastereomers,
  b. separating at least one oxazolidine diastereomer from said mixture.
  c. hydrolyzing said oxazolidine to free the optically active oxo compound, and
  d. recovering said optically active oxo compound.

In carrying out the resolution of the formula LX ketone, there is prepared an oxazolidine by reaction of the ketone with an optically active ephedrine, e.g. d- or l-ephedrine, or d- or l-pseudoephedrine. Approximately equimolar quantities of the reactants are employed in a solvent such as benzene, isopropyl ether, or dichloromethane. The reaction proceeds smoothly over a wide range in temperature, for example 10° to 80° C., although for some reactants the range 20° to 30° C., is preferred for convenience. The reaction occurs quickly, within minutes, whereupon the solvent is removed, preferably under vacuum. The product consists of the diastereomers of the ketone-ephedrine product, i.e. the oxazolidines. At least one of the diastereomers is separated by methods known in the art, including cyrstallization and chromatography. In this instance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the ketone.

The mother liquor from the recrystallized diastereomer contains the optical isomer having opposite configuration. A preferred method for isolating this second diastereomer, however, is to prepare the oxazolidine of the racemic ketone using ephedrine of the opposite configuration to that first employed above, and thereafter recrystallizing as above. Finally, hydrolysis and recovery yield the resolved formula LX ketone in opposite configuration to that first obtained above.

Each optically active ketone can be converted to an aldehyde of the formula

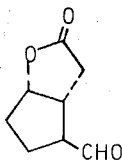

or the mirror image thereof, using the procedures of Corey et al., Tetrahedron Letters 49, 4753 (1971). That ketone is especially useful which yields the formula X aldehyde which produces the 11-deoxy prostaglandin analogs having the natural configuration.

Likewise, the above process of resolution applied to the racemate containing the formula X aldehyde yields the optically active formula X aldehyde which produces the 11-deoxy prostaglandin analogs having the natural configuration.

As discussed above, the processes herein described inclusive, lead variously to acids ($R_1$ is hydrogen) or to esters.

When the alkyl ester has been obtained and an acid is desired, saponification procedures, as known in the art for F-type prostaglandins may be used.

Alternatively enzymatic processes for transformation of esters to their acid forms may be used by methods known in the art. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N. Y., Vol. 8, pp. 389–394 (1954).

An alternative method for alkyl, cycloalkyl or aralkyl esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of this invention are prepared by methods known in the art. For example, the prostaglandin-type free acid may be silylated by methods known in the art, thereby protecting the free hydroxy groups. Since the silylation may transform the carboxy acid moiety, —COOH, into a silyl ester derivative, a brief treatment of the silylated compound with water may be necessary to transform the silylated compound into free acid form. This free acid may then be reacted with oxalyl chloride to provide an acid chloride. The acid chloride may be esterified by reacting it with phenol or the appropriate substituted phenol to give a silylated phenyl or substituted phenyl ester. Finally, the silyl groups are replaced by free hydroxy moieties by hydrolysis under acidic conditions. For this purpose dilute acetic acid may be advantageously used.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carred out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water of addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The invention can be more fully understood by the following preparations and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard.

"Brine", herein, refers to an aqueous saturated sodium chloride solution.

PREPARATION 1

Dimethyl 2-oxo-3,3-dimethylheptylphosphonate

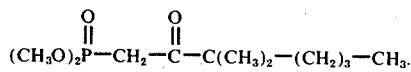

n-Butyllithium (130 ml. of 1.6 M solution) is slowly added to a solution of dimethyl methylphosphonate (25.6 g.) in 475 ml. of tetrahydrofuran (THF) at about −65° C. To the mixture is added a solution of ethyl 2,2-dimethyl-hexanoate (20.24 g.) in 50 ml. of THF, and the resulting mixture is stirred at about −70° C. for 2 hr. Then, 16 ml. of acetic acid is added, and the mixture is concentrated under reduced pressure. The residue is mixed with dichloromethane (about 400 ml.) and water (about 50 ml.) shaken, and separated. The organic phase is dried over magnesium sulfate and concentrated. Distillation yields the title compound.

Following the procedure of Preparation 1, but using in place of ethyl 2,2-dimethyl-hexanoate either methyl 2,2-dimethyl-butanoate, methyl 2,2-dimethyl-pentanoate, methyl 2,2-dimethyl-hexanoate, methyl 2,2-dimethyl-octanoate, methyl 2-methyl-hexanoate, methyl 2-methyl-butanoate, methyl-2-methyl-pentanoate, methyl-2-methyl-heptanoate, methyl-2-methyl octanoate, methyl hexanoate, methyl butanoate, methyl pentanoate, methyl heptanoate, or methyl octanoate, there is obtained respectively: dimethyl 2-oxo-3,3-dimethyl-pentylphosphonate, dimethyl 2-oxo-3,3-dimethylhexylphosphonate, dimethyl 2-oxo-3,3-dimethyloctylphosphonate, dimethyl 2-oxo-3,3-dimethylnonylphosphonate, dimethyl 2-oxo-3-3methyl-heptanoate, dimethyl-2-oxo-3-3methyl-epntylphosphonate, dimethyl-2-oxo-3-methyl-hexylphosphonate, dimethyl 2-oxo-3-methyl-octylphosphonate, dimethyl 2-oxo-3-methyl-nonyl-phosphonate, dimethyl 2-oxo-heptylphosphonate, dimethyl 2-oxo-pentyl phosphonate, dimethyl 2-oxo-hexylphosphonate, dimethyl 2-oxo-octylphosphonate, or dimethyl 2-oxo-nonylphosphonate.

PREPARATION 2

3-Carboxypropyl triphenylphosphonium bromide, Br(C₆H₅)₃P(CH₂)₃COOH

Triphenylphosphine (156.8 g.) and 4-bromobutyric acid (100 g.) are heated in 125 ml. of benzene at reflux for 18 hr. The crystalline product is filtered off, washed with benzene, and recrystallized from ethanol-acetonitrile-diethyl ether.

PREPARATION 3

5-Carboxypentyltriphenylphosphonium bromide, Br(C₆H₅)₃P(CH₂)₅COOH

Triphenylphosphine (156 g.) and 6-bromohexanoic acid (115 g.) are heated in 125 ml. of benzene at reflux for 18 hr. The crystalline product is filtered off, washed with benzene, and recrystallized from methanol-diethyl ether.

PREPARATION 4

5α-Hydroxy-2β-(3-oxo-4,4-dimethyl-trans-1-octenyl)-1α-cyclopentaneacetic acid, γ-lactone (Formula XI: L₁ is

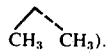

Refer to Chart A. There is first prepared a solution of dimethyl 2-oxo-3,3-dimethylheptylphosphonate (Preparation 1). The phosphonate (10.8 g.) in dry tetrahydrofuran (40 ml.) is added in portions over 21 minutes to a stirred mixture of sodium hydride (1.66 g. of 57 percent) in mineral oil (0.95 g.) and dry tetrahydrofuran (75 ml.) under nitrogen and previously cooled to 2° C. Stirring is continued at 25° C. for 40 min. The mixture is cooled to 2° C. There is then added a dichloromethane solution of the formula X aldehyde (P. Crabbe and A. Guzman, Tetrahedron Lett. No. 2,115 (1972), for racemic) over a 10 min. period. The mixture is stirred at 25° C. for 2.25 hr. and then acetic acid (4 ml.) is added dropwise. The mixture is washed with water (2 × 100 ml.), dried with magnesium sulfate and concentrated under reduced pressure. The residue is dissolved in dichloromethane and chromatographed on silica gel (800 g.) by elution with 5 percent acetone in dichloromethane. Those fractions shown by TLC to contain pure product are combined and concentrated to an oil of the formula XI compound; mass spectral peaks at 278, 223, 222, 180, 179, 162, and 99; infrared spectral absorptions at 1775, 1685, 1625, 1165, 1040, 985, and 900 cm.⁻¹; NMR peaks at 0.7–1.1 (broad triplet, 3H), 1.1–2.8 (broad multipled with a singlet at 1.11, 2OH), 4.85–5.15 (broad, 1H), and 6.3–6.8 (multiplet, 2H) δ.

Following the procedure of Preparation 4, but replacing the 2-oxo-3,3-dimethylheptylphosphonate of that preparation with a 2-oxo-3-dimethylheptylphosphonate, there is obtained the corresponding formula XI cmpound wherein L₁ is

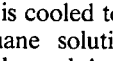

and

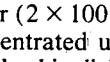

Following the procedure of Preparation 4, but replacing the 2-oxo-3,3-dimethyl-phosphonate of that preparation with a 2-oxo-3,3-dimethyl alkylphosphonate, 2-oxo-3-methyl-alkylphosphonate, or 2-oxo-alkylphosphonate described in the paragraph following Preparation 1, there is prepared the corresponding 5α-hydroxy-2β-(3-oxo-4,4-dimethyl-trans-1-alkenyl)-1α-cyclopentaneacetic acid γ-lactone, 5α-hydroxy-2β-[3-oxo(4R)-, (4S)-, or (4RS)-4-methyl-trans-1-alkenyl]-1α-cyclopentaneacetic acid γ-lactone, or 5α-hydroxy-2β-(3-oxo-trans-1-alkenyl)-1α-cyclopentaneacetic acid γ lactone.

2-Oxo-3-methyl-alkylphosphonates exist in either of two optically active forms (+ or −) or their racemic (dl) mixture. An optically active phosphonate is obtained by starting with an appropriate optically active isomer of the aliphatic acid. Methods of resolving these acids are known in the art, for example by forming salts with an optically active base such as brucine, separating the resulting diastereomers, and recovering the acids.

PREPARATION 5

5α-Hydroxy-2β(3α-hydroxy-4,4-dimethyl-trans-1-octenyl)-1α-cyclopentaneacetic acid, γ-lactone and its 3β-epimer (Formula XII: L₁ is

M₅ is either

or

R₇ is —(CH₂)₃—CH₃ and Y is trans-CH=CH—)

To a mixture of zinc borohydride prepared from zinc chloride (anhydrous, 3.88 g.) and sodium borohydride (1.21 g.) in dry 1,2-dimethoxyethane (75 ml.) under nitrogen stirred at 25° C. for 2 hr. and then cooled to −33° C., is added the formula XI compound (2.65 g.) in 40 ml. of 1,2-dimethoxyethane. The mixture is stirred for 2.5 hr. at 0° C., warmed to 25° C. and stirred until the reaction is complete as monitored by TLC. The mixture is cooled to 0° C. and 9 ml. of water is added dropwise. After hydrolysis is complete, ethyl acetate (100 ml.) is added, the mixture is filtered and the filter cake is washed with 200 ml. of ethyl acetate. The combined filtrate and washing is washed with 100 ml. of water and 100 ml. of brine, dried with magnesium sulfate and concentrated to yield 2.95 g. of oily product. The oil is chromatographed on silica gel (300 g.), eluted with 1 percent, 2 percent, and 75 percent acetone-dichloromethane, to separate the α and β isomers. Fractions containing the α and β isomers, as shown by TLC, are combined and concentrated. There is obtained 0.47 g. of the α isomer of formula XII compound; mass spectral peaks at 281, 263, 182, 164, 138, 135, and 99; infrared spectral absorptions at 3480, 1765, 1660, 1200, 1165, 1035 and 975 cm.⁻¹; NMR peaks at 0.7–1.1 (triplet, 9H), 1.1–2.7 (broad multiplet, 15H), 3.7–3.9 (multiplet, 1H), 4.8–5.1 (broad, 1H), and 5.5–5.65 (multiplet, 2H) δ.

Following the procedure of Preparation 5, but replacing 5α-hydroxy-2β-(3 oxo-4,4-dimethyl-trans-1-octenyl)-1α-cyclopentaneacetic acid γ lactone used therein with the 5α-hydroxy-2β-(3-oxo-4,4-dimethyl-trans-1-alkenyl), 2β-(3-oxo-4-methyl-trans-1-alkenyl)-, or 2β-(3-oxo-trans-1-alkenyl)-1α-cyclopentaneacetic acid γ lactones described following Preparation 4, there are obtained the corresponding 5α-hydroxy-2β-(3α-hydroxy-4,4-dimethyl-trans-1-alkenyl)-1α-cyclopentaneacetic acid γ lactones, 5α-hydroxy-2β-[3α-hydroxy-(4R)-, or (4RS)-methyl-trans-1-alkenyl]-1α-cyclopentaneacetic acid γ lactones, or 5α-hydroxy-2β-(3α-hydroxy-trans-1-alkenyl)-1α-cyclopentaneacetic acid γ lactones, and their corresponding 3β epimers.

PREPARATION 6

5α-Hydroxy-2β-(3α-hydroxy-3-methyl-4,4-dimethyl-trans-1-octenyl)-1α-cyclopentaneacetic acid, γ lactone and its 3β-epimer. (Formula XII: L₁ is

M₅ is a mixture of

and

R₇ is —(CH₂)₃—CH₃, and Y is trans-CH=CH—)

Refer to Chart A. A solution of the formula XI compound (Preparation 4, 0.3 g.) in 25 ml. of dry benzene under a nitrogen atmosphere is treated with stirring with 1.35 ml. of a 1.69 M solution of trimethylaluminum in toluene. The reaction is monitored by silica gel thin layer chromatography. After about 5 hr. an additional 1.5 ml. of trimethylaluminum solution, as above, is added. At 15 min. intervals, the progress of the reaction is monitored by thin layer chromatography. When chromatographic examination indicates that substantially all the starting material has been consumed (approximately 30 min.), the mixture is cooled in an ice bath, while cautiously adding 30 ml. of saturated aqueous sodium chloride. A solid separates. Then, 50, ml. of diethyl ether is added and the mixture is filtered. The filter cake is washed well with diethyl ether. The combined filtrate and washings are shaken and the layers separated. The aqueous layer is extracted with diethyl ether. The combined organic layers are dried using magnesium sulfate. Evaporation of the solvent under reduced pressure 40° C. yields residue which is chromatographed on 50 g. of silica gel. The title compound is thereby obtained.

Following the procedure of Preparation 6, but using in place of 5α-hydroxy-2β-(3-oxo-4,4-dimethyl-trans-1-octenyl-1α-cyclopentaneacetic acid γ lactone used therein, the 5α-hydroxy-2β-(3-oxo-4,4-dimethyl-trans-1-alkenyl)-1α-cyclopentaneacetic acid γ lactones, 5α-hydroxy-2β-(3-oxo-4-methyl-trans-1-alkenyl)-1α-cyclopentaneacetic acid γ lactones, or 5α-hydroxy-2β-(3-oxo-trans-1-alkenyl)-1α-cyclopentaneacetic acid γ lactones described following Preparation 4, there are obtained the corresponding 5α-hydroxy-2β-[(3RS)-3-hydroxy-3-methyl-4,4-dimethyl-trans-1-alkenyl]-1α-cyclopentaneacetic acid γ lactones, 5α-hydroxy-2β-[(3RS)-3-hydroxy-3-methyl-(4R)-, (4S)-, or (4RS)-4-methyl-trans-1-alkenyl-1α-cyclopentaneacetic acid γ lactones, or 5α-hydroxy-2β-[(3RS)-3-hydroxy-3-methyl-trans-1-alkenyl]-1α-cyclopentaneacetic acid γ lactones.

PREPARATION 7

5α-Hydroxy-2β-(3α-methoxy-4,4-dimethyl-trans-1-octenyl)-1α-cyclopentaneacetic acid, γ lactone and its 3β-epimer (Formula XII: L₁ is

M₅ is either

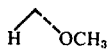

or

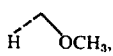

R₇ is —(CH₂)₃—CH₃, and Y is trans-CH=CH—)

A mixture of the formula XII 3α-hydroxy compound of Preparation 5 (2.0 g.), silver oxide (4.0 g.), methyl iodide (50 ml.) and benzene (150 ml.) is stirred and heated at reflux for 60 hr. The resulting mixture is cooled and filtered, and the filtrate is concentrated. The residue is subjected to silica gel chromatography to yield the title compound.

The 3β-hydroxy compound of Preparation 5 yields the corresponding 3β-methoxy product.

Following the procedure of Preparation 7, but using in place of 5α-hydroxy-2β-(3α-hydroxy-4,4-dimethyl-trans-1-octenyl)-1α-cyclopentaneacetic acid γ lactone or its 3β-epimer, the other 5α-hydroxy-2β-(3-hydroxy-4,4-dimethyl, 4-methyl, or unsubstituted-trans-1-alkenyl)-1α-cyclopentaneacetic acid γ lactones described hereinabove there are obtained the corresponding 5α-hydroxy-2β-(3α-methoxy-4,4-dimethyl-, 4-methyl-, or unsubstituted-trans-1-alkenyl)-1α-cyclopentaneacetic acid γ lactones, or their respective 3β-epimers.

PREPARATION 8

5α-Hydroxy-2β-(3α-hydroxy-4,4-dimethyl-trans-1-octenyl)-1α-cyclopentaneacetaldehyde, γ lactol, tetrahydropyranyl ether and its 3β-epimer (Formula XIV: L₁ is

M₆ is either

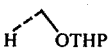

or

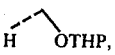

R₇ is —(CH₂)₃—CH₃, and Y is trans-CH=CH—)

a. A mixture of the formula XII compound (α isomer from Preparation 5) dihydropyran (0.67 g.), a few crystals of pyridine hydrochloride and dichloromethane (20 ml.) is stirred under nitrogen for 66 hr. The mixture is concentrated to obtain a mixture containing the formula XIII compound wherein M₆ is

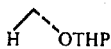

b. To the product of a. in toluene (40 ml.) at —78° C., is added dropwise, while stirring, diisobutylaluminum hydride (2.7 ml. in 24.3 ml. toluene. Stirring is continued at —78° C. for 1 hr. and then a solution of tetrahydrofuran (9 ml.) and water (6 ml.) is added dropwise over 15 minutes. After the mixture is allowed to warm to room temperature, it is filtered and the filter cake is washed with brine, dried and concentrated to yield 0.60 g. of the lactol of the formula XIV.

Following the procedure of Preparation 8, but using in place of 5α-hydroxy-2β-(3α-hydroxy-4,4-dimethyl-trans-1-octenyl)-1α-cyclopentaneacetic acid γ lactone or its 3β-epimer, the various 5α-hydroxy-2β-[(3S)- or (3R)-3-hydroxy-4,4-dimethyl-, 4-methyl-, or unsubstituted-trans-1-alkenyl]-1α-cyclopentaneacetic acid γ lactones described following Preparation 5, there are obtained the corresponding γ lactol tetrahydropyranyl ether products. Further, following the procedure of Preparation 5, but using in place of the 3α-hydroxy γ lactone therein the (3RS)-3-methyl or 3α- or 3β-methoxy γ lactones, there are obtained the corresponding γ lactols, but as tetrahydropyranyl ethers only when the (3RS)-3-methyl reactant is used.

PREPARATION 9

5α-Hydroxy-2β-(3α-hydroxy-3-methyl-4,4-dimethyl-octyl)-1α-cyclopentaneacetaldehyde, γ lactol, tetrahydropyranyl ether (Formula XIV: Y is —CH₂CH₂—, M₅ is

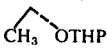

or

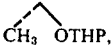

L₁ is

and R₇ is —(CH₂)₃—CH₃ or its 3β-epimer

Refer to Chart D.

A. To a stirred solution of the title compound of Preparation 6 (26.5 g.) in 250 ml. of pyridine under nitrogen, is added 15 ml. of benzoyl chloride at 0° C. The resulting solution is then stirred for 5 hr. at ambient temperature. Thereafter the solution is cooled to 0° C. and 25 ml. of water is added dropwise. The resulting mixture is stirred at 0° C. for an additional 30 min. This mixture is then equilibrated with 1 l. of ethyl acetate and 1 l. of aqueous sulfuric acid and ice. The phases are separated and the aqueous phase extracted with ethyl acetate. The organic extracts are combined, washed with water, and sodium bicarbonate. The organic extracts are combined, washed with brine, dried over sodium sulfate, and evaporated to yield the 3-benzoate.

B. The 3(RS)-benzoate epimeric mixture of part A above is chromatographed on 1800 g. of silica gel slurried in methylene chloride. Elution proceeds with 1 percent, then 2 percent, acetone in methylene chloride. Fractions as shown by thin layer chromatography to contain essentially pure 3(R)- or 3(S)-epimers are obtained.

C. Hydrolysis of the 3-benzoate group proceeds as follows:

A solution of sodium methoxide in methanol is prepared by dissolving one g. of sodium and 170 ml. of anhydrous methanol, with stirring and cooling under a nitrogen atmosphere. This solution is then slowly added to a slurry of 12.8 g. of the reaction product of part B above in 70 ml. of anhydrous methanol under nitrogen. The solution is then stirred at ambient temperature for up to several days, or until thin layer chromatography reveals that a quenched aliquot of the reaction mixture shows essentially all starting material has been consumed. Thereafter the reaction is quenched by addition of the above mixture to a cold equilibrated mixture of 300 ml. of 2 M sodium bicarbonate, ice, and 500 ml. of ethyl acetate. After equilibration, the aqueous phase is separated and extracted with ethyl acetate. Combining and washing the organic extracts with water, followed by drying and evaporation yields crude product. Crude product above may be chromatographed on silica gel to yield the 3α-title lactone or its 3β-epimer.

D. A mixture of 4.0 g. of the reaction product of step C above, 800 mg. of 5 percent palladium-on-charcoal catalyst, and 400 ml. of ethyl acetate are stirred at ambient temperature under 1 atmosphere of hydrogen for 1 hr. Hydrogen uptake proceeds rapidly, and ceases within 1 hr. The progress of the reaction is monitored by silver nitrate impregnated silica gel thin layer chromatography eluting with 100 percent ethyl acetate. When the reaction is complete, the mixture is filtered, washed with ethyl acetate, and evaporated to yield the formula LV lactone.

E. Following the procedure of Preparation 8, the lactone product of part D above is transformed into the title lactol tetrahydropyranyl ether.

Following the procedure of Preparation 8, part A-but using various 5α-hydroxy-2β-[(3RS)-3-hydroxy-3-methyl-4,4-dimethyl, 4-methyl, or unsubstituted-trans-1-alkenyl]-1α-cyclopentane acetic acid, γ lactones described following Preparation 6 are transformed into their corresponding 5α-hydroxy-2β-[(3R)- or (3S)-3-hydroxy-3-methyl-4,4-dimethyl, 4-methyl, or unsubstituted alkyl]-1α-cyclopentaneacetic acid γ lactol tetrahydropyranyl ethers. Further, following the procedure of Preparation 8, parts D and E, but using in place of 5α-hydroxy-2β-[(3RS)-3-hydroxy-3-methyl-4,4-dimethyl-trans-1-octenyl]-1α-cyclopentaneacetic acid, γ lactone, the various lactones described in Preparations 5 and 7 and in the text following Preparations 5 and 7, there are obtained the corresponding saturated 3-methoxy and 3-hydroxy lactol tetrahydropyranyl ethers.

EXAMPLE 1

5α-Hydroxy-2β-(3α-hydroxy-4,4-dimethyl-trans-1-octenyl)-1α-cyclopentanepropionaldehyde δ-Lactol (Formula XVI: $R_7$ is —$(CH_2)_3$—$CH_3$, $L_1$ is

$M_5$ is

and Y is trans CH=CH—) and its 3β-hydroxy epimer

Refer to Chart A. A suspension of methoxymethyltriphenylphosphonium chloride (Levine, J. Am. Chem. Soc. 80, 6150 (1958), 32.4 g.) in 150 ml. of tetrahydrofuran (THF) is cooled to −15° C. and to it is added 69.4 ml. of butyllithium (1.6 M. in hexane) in 45 ml. of THF. After 30 min. there is added a solution of the formula XIV 5α-hydroxy-2β-(3α-hydroxy-4,4-dimethyl-trans-1-octenyl)-1α-cyclopentaneacetaldehyde γ-lactol tetrahydropyranyl ether (Preparation 8, 10.0 g.) in 90 ml. of THF. The mixture is stirred for 1.5 hr., meanwhile warming to about 25° C., and is then concentrated under reduced pressure. The residue is partitioned between dichloromethane and water, and the organic phase is dried and concentrated. This residue is then subjected to chromatography over silica gel, eluting with cyclohexane-ethyl acetate (2:1). Those fractions shown by thin-layer chromatography (TLC) to contain the formula -XV intermediate are combined and concentrated to yield that enol-ether.

The above enol-ether, in 20 ml. of THF, is hydrolyzed with 50 ml. of 66 percent acetic acid at about 57° C. for 2.5 hr. The mixture is concentrated under reduced pressure. Toluene is added to the residue and the solution is again concentrated. Finally the residue is subjected to chromatography on silica gel, eluting with chloroform-methanol (6:1). The title compound is obtained by combining and concentrating suitable fractions.

Following the procedure of Example 1, but using in place of the lactol starting material therein the various lactols described following Preparation 8, in Preparation 9, and following Preparation 9, there are obtained the corresponding 3-methyl, 3-methoxy, or 3β-methoxy δ lactols of this invention.

EXAMPLE 2

5α-Hydroxy-2β-(3α-hydroxy-4,4-dimethyl-trans-1-octenyl)-1α-cyclopentane propionaldehyde, δ lactol, tetrahydropyranyl ether and its 3β-epimer (Formula XIX: Y is trans-CH=CH—, $M_6$ is

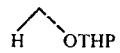

or

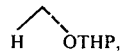

$L_1$ is

and $R_7$ is —$(CH_2)_3$—$CH_3$)

A. Silver oxide is prepared by the addition of silver nitrate (1.14 g.) in water (3 ml.) dropwise to a 2N sodium hydroxide solution (6.8 ml.). A precipitate is formed. To the precipitate in an ice water bath is added the lactol of Example 1 above (1.0 g.) in tetrahydrofuran (4 ml.). The addition is completed and the ice bath removed. The reaction is complete, as evidenced by thin layer chromatography, on silica gel eluting with 90 percent chloroform in methanol. A suspension is removed by filtration and washed with water. The combined washings and filtrate are extracted with ether. The aqueous layer is chilled in an ice bath and acidified with 10 percent potassium bisulfate solution to pH less than 2. The mixture is then extracted with ether. The combined ether extracts are washed with brine, dried with magnesium sulfate, filtered and the solvent evaporated to yield the corresponding formula XVIII lactol.

B. The reaction product of step A above is transformed into the corresponding lactol tetrahydropyranyl ether title compound by following the procedure of Preparation 8 above.

Following the procedure of Example 2, but using in place of the lactol starting material of Example 2, the lactol starting materials described in the text following Example 1, there are prepared the corresponding lactol tetrahydropyranyl ethers.

EXAMPLE 3

4,5-cis-Didehydro-11-deoxy-16,16-dimethyl-PGF$_{1\alpha}$ (Formula XVII: g is 2, R$_1$ is hydrogen, Y is trans-CH=CH—, M$_1$ is

L$_1$ is

and R$_7$ is —(CH$_2$)$_3$—CH$_3$) and its 15-epimer

3-Carboxypropyltriphenylphosphonium bromide (10.6 g., Preparation 1) is added to sodio methylsulfinylcarbanide prepared from sodium hydride (2.08 g., 57%) and 30 ml. of dimethyl sulfoxide, and the resulting Wittig reagent is combined with the lactol of Example 1, in 20 ml. of dimethyl sulfoxide. The mixture is stirred overnight, diluted with about 200 ml. of benzene, and washed with potassium hydrogen sulfate solution. The lower layers are washed with dichloromethane, and the organic phases are combined, washed with brine, dried, and concentrated under reduced pressure. The residue is subjected to chromatography over acid-washed silica gel, eluting with ethyl acetate-isomeric hexanes (3:1). Those fractions shown to contain the desired compound by TLC are combined and concentrated to yield the title compound.

Following the procedures of Example 3, but replacing the lactol of that Example with the corresponding 3β-hydroxy compound obtained following Example 1, there is obtained the corresponding 4,5-cis-didehydro-11-deoxy-15-epi-PGF$_{1\alpha}$ product.

Following the procedures of Example 3, but replacing the lactol starting material therein with the corresponding 3-methyl compound obtained following Example 1, there is obtained the corresponding 4,5-cis-didehydro-11-deoxy15(RS)-15-methyl-PGF$_{1\alpha}$ product.

Following the procedures of Example 3, but replacing the lactol starting material therein with the corresponding 3α- or 3β-hydroxy or 3α- or 3β-methoxy lactols described following Example 1, there is obtained the corresponding 4,5-cis-didehydro-11-deoxy-16-methyl-, 16,16-dimethyl, or 16-unsubstituted-PGF$_{1\alpha}$ or 4,5-cis-didehydro-11-deoxy-16-methyl-, 16,16-dimethyl-, or 15-epi-PGF$_{1\alpha}$ products.

Accordingly, following the procedures of Example 3, but replacing the lactol starting material therein with the various optically active or racemic 3α- or 3β-hydroxy lactols obtained following example 1, there is obtained the corresponding optically active or racemic 4,5-cis-didehydro-11-deoxy-PGF$_{1\alpha}$ or 4,5-cis-didehydro-11-deoxy-15-epi-PGF$_{1\alpha}$ -type product, within the scope of formula XVII, for example:

4,5-cis-didehydro-11-deoxy-19,20-dinor-PGF$_{1\alpha}$
dl-4,5-cis-didehydro-11-deoxy-19,20-dinor-PGF$_{1\alpha}$
4,5-cis-didehydro-11-deoxy-19,20-dinor-15-epi PGF$_{1\alpha}$
dl-4,5-cis-didehydro-11-deoxy-19,20-dinor-15-epi-PGF$_{1\alpha}$
4,5-cis-didehydro-11-deoxy-16-methyl-PGF$_{1\alpha}$
dl-4,5-cis-didehydro-11-deoxy-16-methyl-PGF$_{1\alpha}$
4,5-cis-didehydro-11-deoxy-16-methyl-15-epi-PGF$_{1\alpha}$
dl-4,5-cis-didehydro-11-deoxy-16-methyl-15-epi-PGF$_{1\alpha}$
4,5-cis-didehydro-11-deoxy-16-methyl-20-methyl-PGF$_{1\alpha}$
dl-4,5-cis-didehydro-11-deoxy-16-methyl-20-methyl-PGF$_{1\alpha}$
4,5-cis-didehydro-11-deoxy-16-methyl-20-methyl-15-epi-PGF$_{1\alpha}$
dl-4,5-cis-didehydro-11-deoxy-16-methyl-20-methyl-15-epi-PGH$_{1\alpha}$ Further, following the procedure of Example 3, but using in place of the unsaturated 3-methyl or 3-methoxy δ lactols of Example 1 the 3-methyl, 3-methoxy, or 3-hydroxy saturated lactols of Example 1 there are obtained the corresponding 13,14-dihydro-PGF$_{1\alpha}$ -type products, optionally substituted at C-15 with methyl or methoxy, and optionally substituted at C-16 with 1 or 2 methyl. Further, using the 3β-hydroxy-3-methyl, 3β-methoxy, or 3β-hydroxy saturated δ lactols according to Example 1, there are obtained the corresponding 15-epi-PGF$_{1\alpha}$ -type products.

EXAMPLE 4

4,5-cis-Didehydro-11-deoxy-15-methyl-PGF$_{1\alpha}$, (Formula XVII: g is 2, R$_1$ is hydrogen, Y is trans-CH=CH—, M$_1$ is

L$_1$ is

and R$_7$ is —(CH$_2$)$_3$—CH$_3$) and its 3β-epimer, as free acid or methyl ester Following the procedure of Example 3, but using in place of the lactol starting material therein, 5α-hydroxy-2β-[(3RS)-3-hydroxy-3-methyl-trans-1-octenyl]-1α-cyclopentanepropionaldehyde, δ lactol there is prepared the corresponding 4,5-cis-didehydro-11-deoxy-15(RS)-15-methyl-PGF$_{1\alpha}$ free acid.

A solution of diazomethane (about 50 percent excess) in diethyl ether (25 ml.) is added to a solution of 4,5-cis-didehydro-11-deoxy-15(RS)-15-methyl-PGF$_{1\alpha}$ (obtained above, 50 mg.) in 25 ml. of a mixture of methanol and diethyl ether (1:1). The mixture is left standing at 25° C. for 5 min. and then is concentrated under reduced pressure to the title methyl ester as an epimeric mixture.

The C-15 epimers of the methyl ester obtained above are chromatographed on 150 g. of silica gel. Eluting with dichloromethane-acetic acid-Skellysolve B, those fractions as shown by thin layer chromatography to contain pure 15(R) or 15(S) product are combined.

Each of the 15-epimers so obtained is saponified by reaction with a slight excess of sodium hydroxide in an aqueous-alcoholic solution, followed by acidification with dilute hydrochloric acid and extraction in diethyl ether.

Following the procedure of Example 4, but using in place of the 3-methyl δ lactol starting material therein, the various 3(RS)-3-methyl lactols described following Example 1 there are prepared the corresponding 4,5-cis-didehydro-11-deoxy-15-methyl-16-methyl or 16,16-dimethyl PGF$_{1\alpha}$-type products or their 15-epimers.

Following the procedure of Example 3 or Example 4, but using in place of the (3-carboxypropyl)triphenlphosphonium bromide the compound of Preparation 2, (5-carboxypentyl)-triphenylphosphonium bromide, there are prepared the 2a,2b-dihomo compounds corresponding to the PG-type products described in Examples 3 and 4 and in the text following Examples 3 and 4.

Following the procedure of Example 3, each of the 4,5-cis-didehydro-PGF$_{1\alpha}$-type products obtained following Example 2, including their 15β-epimers and the racemic forms, is transformed to a corresponding methyl ester.

EXAMPLE 5

4,5-cis-Didehydro-11-deoxy-16,16-dimethyl-PGE$_1$
(Formula XXII: R$_1$ is hydrogen R$_7$ is —(CH$_2$)$_3$—CH$_3$, g is 2, M$_1$ is

L$_1$ is

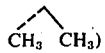

and its 15-epimer and methyl esters

Refer to Chart A.

A. Following the procedure of Example 3, but using in place of the lactol starting material of Example 1, the δ lactol tetrahydropyranyl ether of Example 2, there is prepared 4,5-cis-didehydro-11-deoxy-16,16-dimethyl-PGF$_{1\alpha}$, tetrahydropyranyl ether.

B. A solution of the above tetrahydropyranyl ether (step A) in dichloromethane (4 ml.) is added to a solution of CrO$_3$-pyridine (prepared from 0.26 g. of CrO$_3$ and 0.4 ml. of pyridine in 16 ml. of dichloromethane). The mixture is stirred for 5 min. at about 0° C. and 5 min. at about 25° C., then diluted with 10 ml. of ethyl acetate and filtered through silica gel. The solution, together with rinsings, is concentrated under reduced pressure to yield the formula XXI compound.

C. The product of step B is hydrolyzed in 6 ml. of methanol, 1 ml. of water, and about 0.1 ml. of acetic acid at about 35° C. for 15 min. The volatiles are removed under reduced pressure and the residue is partitioned between dichloromethane and water. The organic phase is separated, dried over sodium sulfate, and concentrated under reduced pressure. The residue is chromatographed on silica gel, eluting with ethyl acetate-Skellysolve B (isomeric hexanes) (4:1). Those fractions containing the title compound free of starting material and impurities are combined and concentrated to yield the title free acid. Mass spectral base peak absorption for the trimethylsilyl derivative is observed at 508.3378 and other mass spectral peaks at 493, 418, 409, 403, 337, and 309.

The title methyl ester is prepared as described in Example 4. Mass spectral base peak absorption for the trimethylsilyl derivative is observed at 450.3135 and other mass spectral peaks at 435, 419, 393, 360, 351, and 329.

Following the procedure of Example 5, but using in place of the lactol starting material of Example 2, the various δ lactols described following Example 2 there are prepared the corresponding PGE$_1$-type compounds. For the 3(RS)-3-methyl lactols the corresponding 15-methyl-PGE$_1$-type compounds are prepared by following the procedure of Example 4 in place of the procedure of Example 5, part A.

Further, following the procedure of Example 5, there are prepared 2a,2b-dihomo-PGE$_1$-type compounds of this invention by use of 5-carboxypentyltriphenylphosphonium bromide in place of 3-carboxypropyltriphenylphosphonium bromide as used in Example 5, part A.

EXAMPLE 6

4,5-cis-Didehydro-11-deoxy-15-methyl-16-methyl-PGF$_{1\alpha}$, Methyl Ester

Refer to Chart C.

A. A solution of 4,5-cis-didehydro-16-methyl-11-deoxy-PGF$_{1\alpha}$, methyl ester (formula XLIV, 0.5 g.) in 24 ml. of dioxane is stirred at 50° C. for 24 hr., cooled to room temperature, and filtered. The filter cake is washed with tetrahydrofuran, and the filtrate and wash are combined and concentrated under reduced pressure. The residue is taken up in dichloromethane and washed with brine, than dried over sodium sulfate and concentrated under reduced pressure. The residue is chromatographed on silica gel, eluting with 2-10 percent ethanol in dichloromethane. Fractions shown by TLC to contain the desired product are combined and concentrated to give the formula XLV 15-oxo intermediate.

B. The product of step A is dissolved in anhydrous ether and 110 percent of the theoretical amount of 3 M methyl magnesium bromide in ether is added. The mixture is allowed to stand at least 20 min. at about 25° C. and poured into 100 ml. of saturated aqueous ammonium chloride. The ether layer is separated, the aqueous layer is extracted with ether, and the ether extracts are combined and washed with brine, dried over sodium sulfate, and evaporated under reduced pressure. The residue is dissolved in 300 ml. of ethanol and 30 ml. of water containing 3 drops of glacial acetic acid, and the mixture is stirred for 2 hr. at about 25° C.

The mixture is concentrated under reduced pressure to an aqueous residue and the residue is extracted with dichloromethane. The dichloromethane extract is evaporated under reduced pressure to give a residue which is chromatographed over silica gel, eluting with 5–10 percent ethanol in dichloromethane. Fractions shown by TLC to contain the desired product are combined and concentrated to yield the desired formula IX title compound. Other fractions yield the 15-epimer corresponding to formula XLVII.

EXAMPLE 7

4,5-cis-Didehydro-11-deoxy-16,16-dimethyl-PGF$_{1\beta}$
(Formula XXIII: $g$ is 2, $R_1$ is hydrogen, Y is trans-CH=CH—, $M_1$ is

C is

and $R_7$ is —(CH$_2$)$_3$—CH$_3$)

Refer to Chart A. A solution of sodium borohydride (300 mg.) in 6 ml. of ice-cold methanol is added to a solution of 4,5-cis-didehydro-11-deoxy-16,16-dimethyl-PGE$_1$, (Example 5, 650 mg.) in 30 ml. of methanol at −5° C. The mixture is stirred for 0.5 hr. at 0° C. and 5 ml. of acetone is added, after which the mixture is stirred for 5 min. and made slightly acid with acetic acid. The mixture is concentrated under reduced pressure until most of the methanol and acetone are removed, then the residue is extracted with dichloromethane. The extract is washed with water, dilute aqueous sodium bicarbonate, and brine, then dried over sodium sulfate and evaporated under reduced pressure to give a residue. This residue is chromatographed over silica gel, eluting with 2–10 percent ethanol in ethyl acetate. Those fractions containing the title compound free of starting material and impurities, as shown by TLC, are combined and concentrated to yield the formula XXIII product.

Following the procedure of Example 7, but using in place of the PGE$_1$-type starting material therein, the various PGE$_1$-type compounds described in Example 5 and the text following Example 5, there are prepared the corresponding PGF$_{1\beta}$-type compounds.

EXAMPLE 8 cis-4,5-Didehydro-11-deoxy-16-methyl-PGE$_1$
(Formula XXXV: $M_1$ is

$R_7$ is —(CH$_2$)$_3$—CH$_3$, Y is trans-CH=CH—, L$_1$ is

and

and R$_1$ is hydrogen)

Refer to Chart B

A. To a solution of cis-4,5-didehydro-16-methyl-PGA$_1$, methyl ester (see Netherlands Patent 7305434, Derwent No. 696654) (0.77 g.) in pyridine (5 ml.) is added acetic anhydride (1.5 ml.). The mixture is stirred for 4 hr. under nitrogen, water (50 ml.) is added and the mixture is stirred for 55 min. The mixture is extracted with ethyl acetate, the combined extracts are washed, dried and concentrated to yield an oil formula XXXII wherein the blocking group M$_7$ is —OCOCH$_3$.

B. To a stirred solution of the oil of step A dissolved in methanol (25 ml.) at −20 C. under nitrogen there is added a solution of sodium borohydride (2 g.) in 5 ml. of water and 20 ml. of methanol. The mixture is stirred at −20° C. for 20 min. and 3.5 ml. of acetic acid is added cautiously. The mixture is concentrated and then 50 ml. of water is added and the pH of the mixture is adjusted to about pH 3 with citric acid. The mixture is extracted with dichloromethane, the combine extracts are washed with water and brine, dried and concentrated, to yield the formula XXXIII compound.

C. To a solution of the oil of step B dissolved in acetone (15 ml.) at −20° C., there is added dropwise with stirring over a one minute period 1.5 ml. of Jones reagent (21 g. chromium trioxide/60 ml. water/17 ml. concentrated sulfuric acid). The mixture is stirred at −20° C. for 20 min., then 1.5 ml. of isopropanol is added and the mixture is stirred at −20° C. for 10 min. The mixture is diluted with 50 ml. of water and extracted with ether. The combined extracts are washed with water and brine, dried and concentrated. The residue is chromatographed on a silica gel column (70 g.) eluting with 1 percent acetone-dichloromethane. Those fractions shown by TLC to contain the 11-deoxy-PGE$_1$-type alkanoate are combined and concentrated.

D. To a solution of the product of step C dissolved in methanol (15 ml.), there is added sodium hydroxide (0.5 g.) in 3 ml. of water, and the mixture is stirred at 25° C. for 17 hr. The mixture is acidified with 10 ml. of 3N hydrochloric acid, and then concentrated to an aqueous residue. The residue is diluted with 25 ml. of water and extracted with ether. The combined extracts are washed with brine, dried and concentrated. The residue is chromatographed on acid washed silica gel, eluting with 30 percent ethyl acetate-hexane. Those fractions shown by TLC to contain the title compound are combined to give the title compound.

EXAMPLE 9 cis-4,5-didehydro-11-Deoxy-16,16-dimethyl-PGE$_1$, Adamantanamine salt

A mixture of cis-4,5-didehydro-11-deoxy-16,16-dimethyl-PGE$_1$ (0.34 g.) and adamantanamine (0.127 g.) in 33 ml. of diethyl ether is concentrated, with sufficient hexane to cause turbidity, to 10 ml. An oily phase separates, which, when chilled yields a solid. The title compound is obtained by purification.

We claim:
1. A compound of the formula

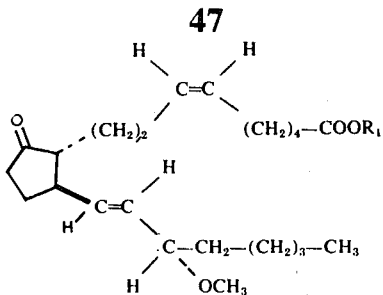

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

2. A compound of the formula

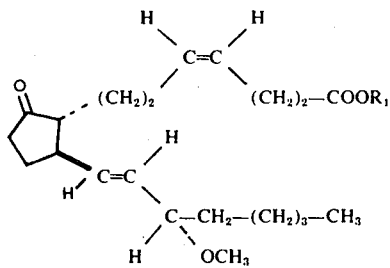

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

3. cis-4,5-Didehydro-11-deoxy-PGE$_1$, 15-methyl ether, methyl ester, a compound according to claim 2.

4. A compound of the formula

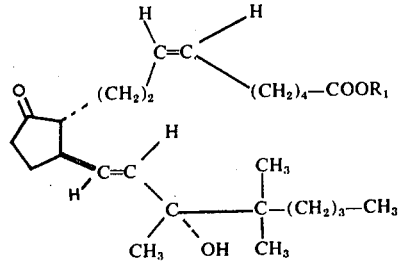

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2 or 3 chloro or alkyl of one to 4 carbon atoms, inclusive, or a pharmacologically acceptable cation.

5. A compound of the formula

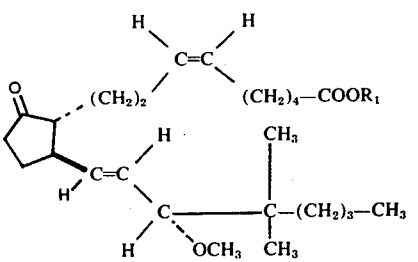

or a mixture comprising that compound and the enantiomer thereof;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

6. A compound of the formula

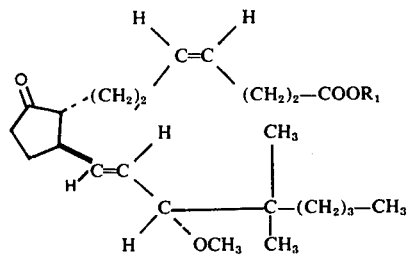

or a mixture comprising that compound and the enantiomer thereof;

wherein $R_1$ is hydrogen, alkyl of one to 12 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

7. cis-4,5-Didehydro-11-deoxy-16,16-dimethyl-PGE$_1$, 15-methyl ether, methyl ester, a compound according to claim 6.

* * * * *

UNITED STATES PATENT OFFICE
CERTIFICATE OF CORRECTION

Patent No. 3,987,072  Dated October 19, 1976

Inventor(s) Gordon L. Bundy and Norman A. Nelson

It is certified that error appears in the above-identified patent and that said Letters Patent are hereby corrected as shown below:

Chart A, appearing in columns 12-15 should read as follows:

Chart A

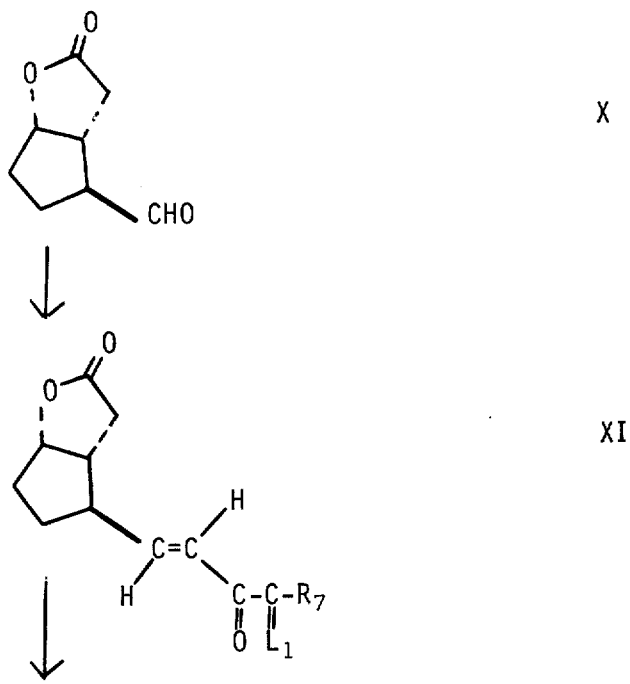

UNITED STATES PATENT OFFICE
CERTIFICATE OF CORRECTION

Patent No. 3,987,072    Dated October 19, 1976

Inventor(s) Gordon L. Bundy and Norman A. Nelson

It is certified that error appears in the above-identified patent and that said Letters Patent are hereby corrected as shown below:

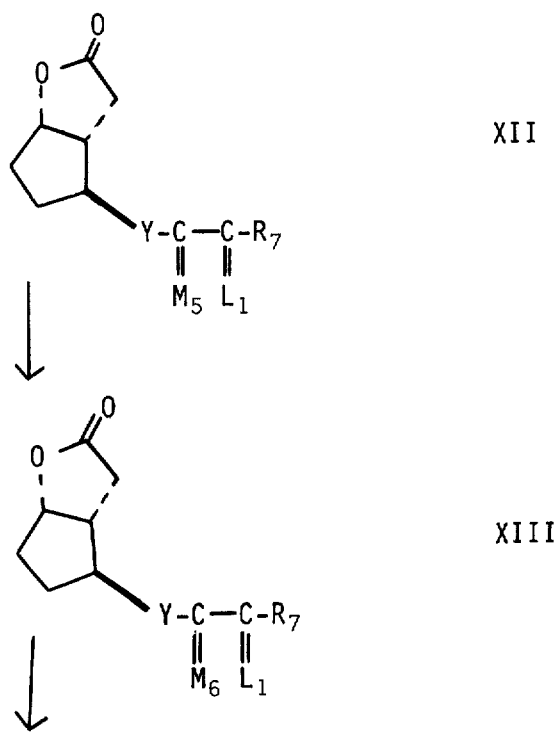

XII

XIII

UNITED STATES PATENT OFFICE
CERTIFICATE OF CORRECTION

Patent No. 3,987,072  Dated October 19, 1976

Inventor(s) Gordon L. Bundy and Norman A. Nelson

It is certified that error appears in the above-identified patent and that said Letters Patent are hereby corrected as shown below:

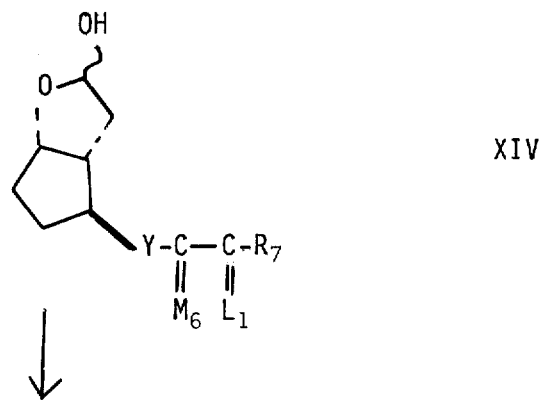

XIV

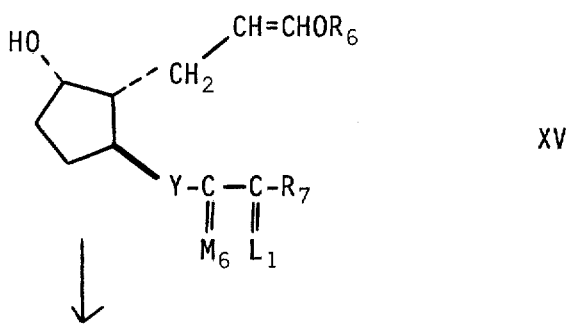

XV

UNITED STATES PATENT OFFICE
CERTIFICATE OF CORRECTION

Patent No. 3,987,072     Dated October 19, 1976

Inventor(s) Gordon L. Bundy and Norman A. Nelson

It is certified that error appears in the above-identified patent and that said Letters Patent are hereby corrected as shown below:

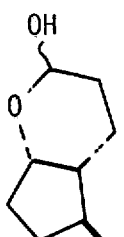
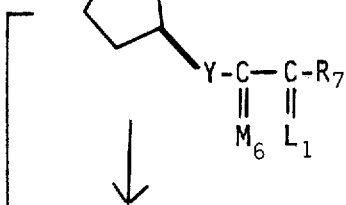
XVI
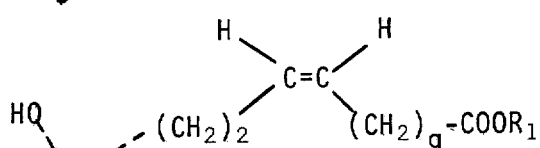
XVII
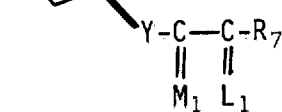

UNITED STATES PATENT OFFICE
CERTIFICATE OF CORRECTION

Patent No. 3,987,072　　　　　Dated October 19, 1976

Inventor(s) Gordon L. Bundy and Norman A. Nelson

It is certified that error appears in the above-identified patent and that said Letters Patent are hereby corrected as shown below:

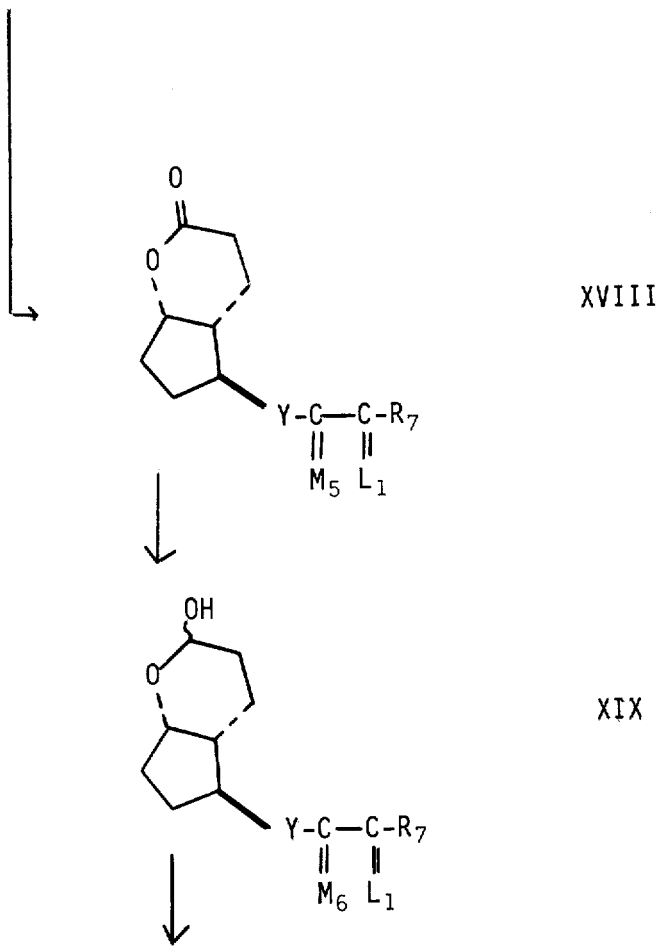

UNITED STATES PATENT OFFICE
CERTIFICATE OF CORRECTION

Patent No. 3,987,072　　　　　　Dated October 19, 1976

Inventor(s) Gordon L. Bundy and Norman A. Nelson

It is certified that error appears in the above-identified patent and that said Letters Patent are hereby corrected as shown below:

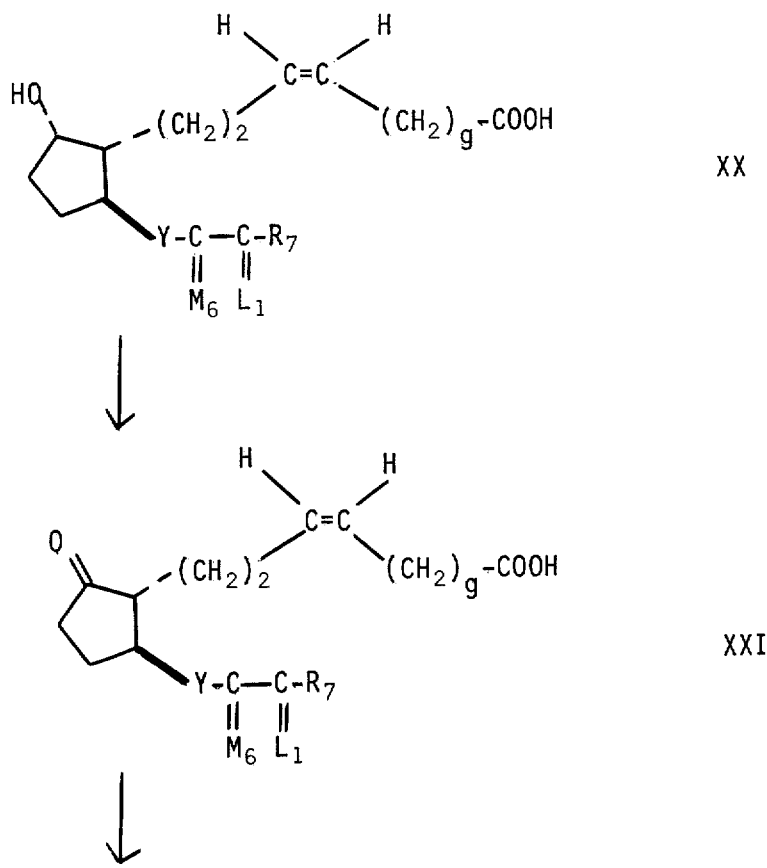

UNITED STATES PATENT OFFICE
CERTIFICATE OF CORRECTION

Patent No. 3,987,072  Dated October 19, 1976

Inventor(s) Gordon L. Bundy and Norman A. Nelson

It is certified that error appears in the above-identified patent and that said Letters Patent are hereby corrected as shown below:

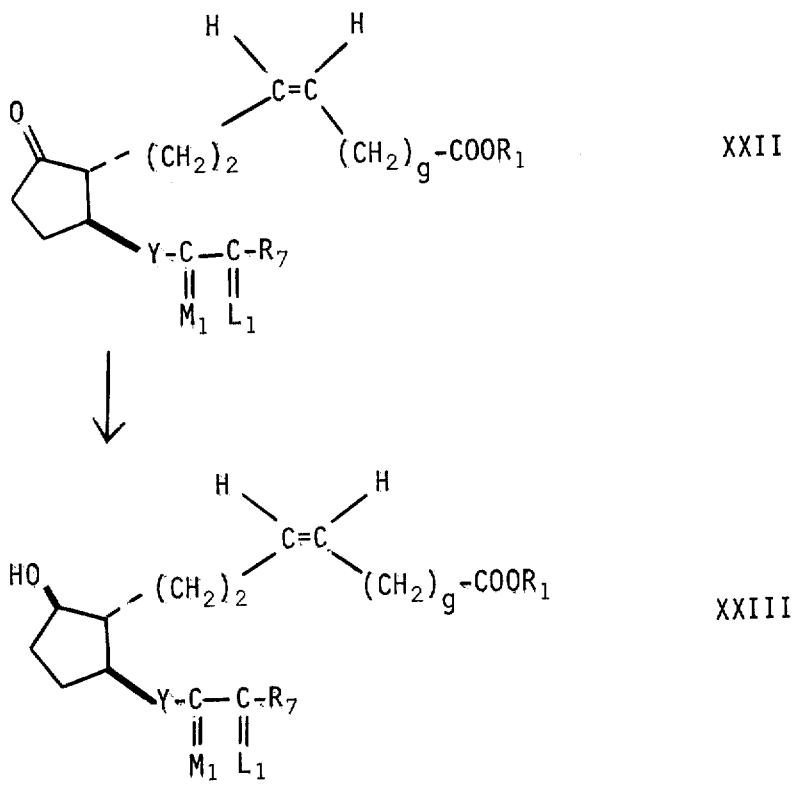

UNITED STATES PATENT OFFICE
CERTIFICATE OF CORRECTION

Patent No. 3,987,072                    Dated October 19, 1976

Inventor(s) Gordon L. Bundy and Norman A. Nelson

It is certified that error appears in the above-identified patent and that said Letters Patent are hereby corrected as shown below:

Chart B, appearing in column 21, should read as follows:

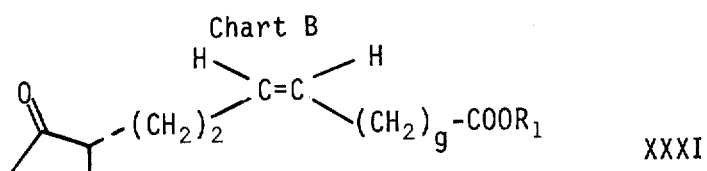

XXXI

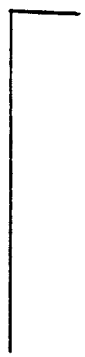

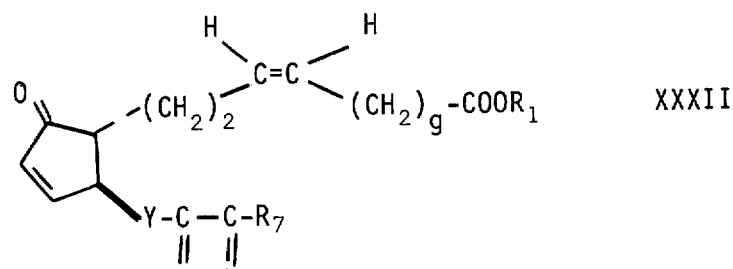

XXXII

UNITED STATES PATENT OFFICE
CERTIFICATE OF CORRECTION

Patent No. 3,987,072          Dated October 19, 1976

Inventor(s) Gordon L. Bundy and Norman A. Nelson

It is certified that error appears in the above-identified patent and that said Letters Patent are hereby corrected as shown below:

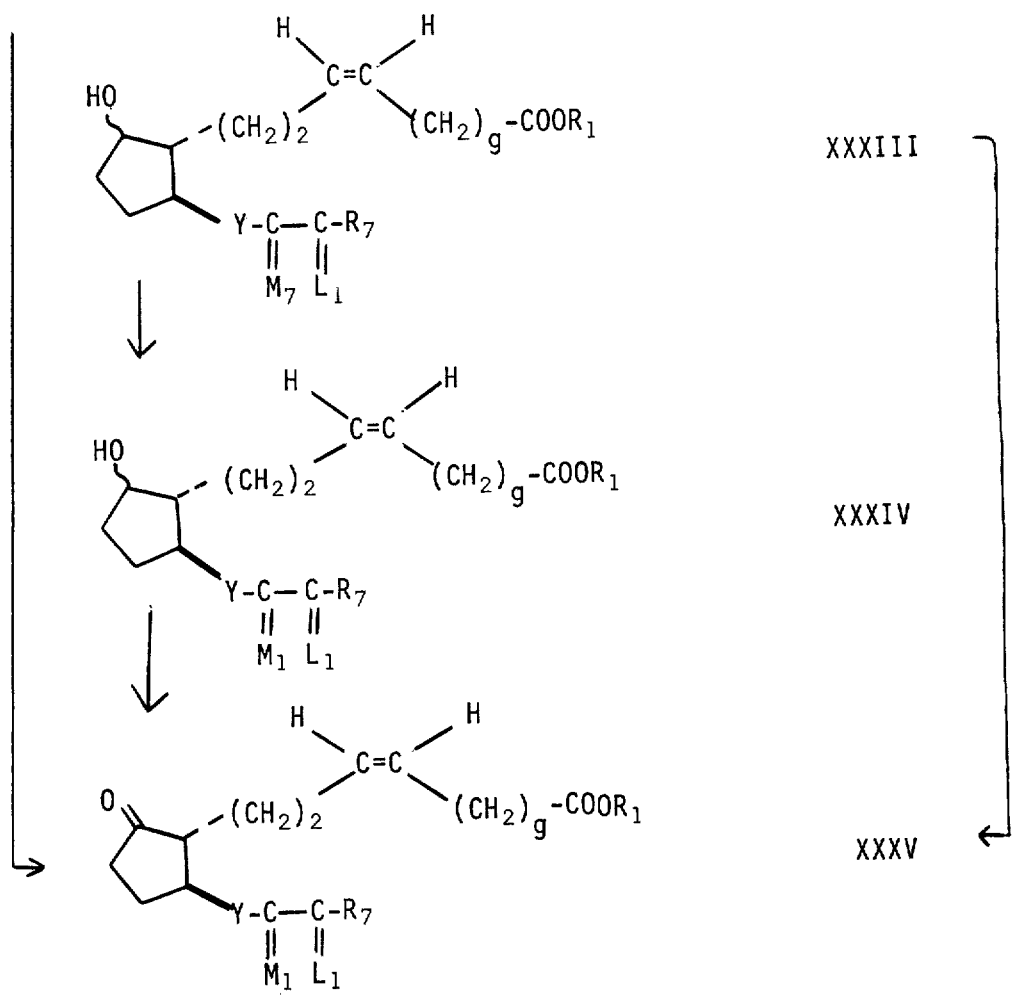

UNITED STATES PATENT OFFICE
CERTIFICATE OF CORRECTION

Patent No. 3,987,072          Dated    October 19, 1976

Inventor(s)    Gordon L. Bundy and Norman A. Nelson

It is certified that error appears in the above-identified patent and that said Letters Patent are hereby corrected as shown below:

Chart C, appearing in Columns 26 and 27, should read as follows:

Chart C

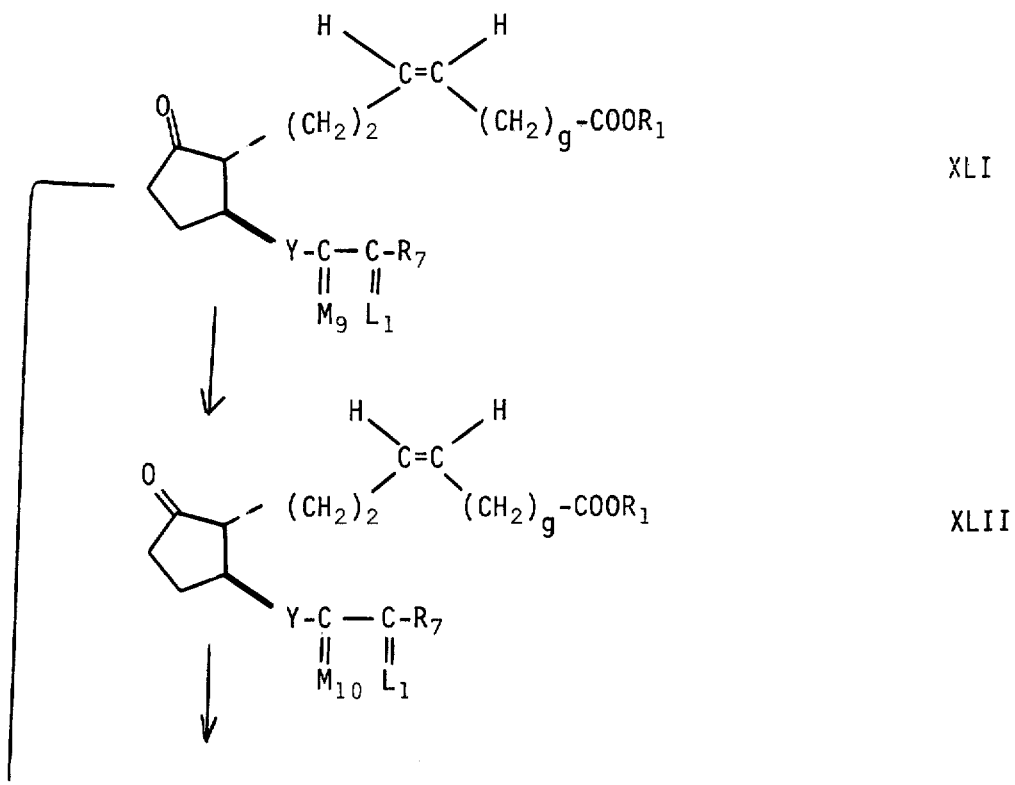

UNITED STATES PATENT OFFICE
CERTIFICATE OF CORRECTION

Patent No. 3,987,072　　　　　　Dated October 19, 1976

Inventor(s) Gordon L. Bundy and Norman A. Nelson

It is certified that error appears in the above-identified patent and that said Letters Patent are hereby corrected as shown below:

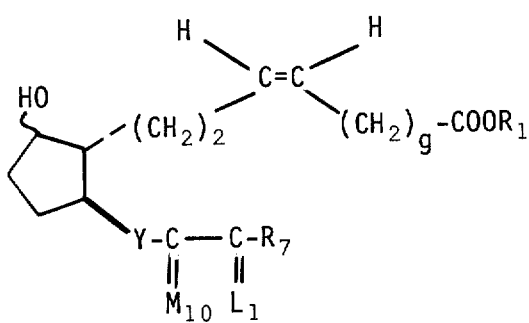

XLIII

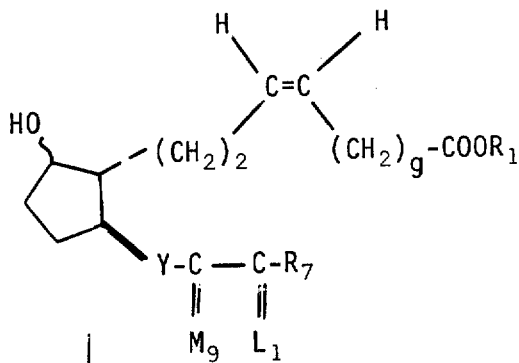

XLIV

UNITED STATES PATENT OFFICE
CERTIFICATE OF CORRECTION

Patent No. 3,987,072     Dated  October 19, 1976

Inventor(s)  Gordon L. Bundy and Norman A. Nelson

It is certified that error appears in the above-identified patent and that said Letters Patent are hereby corrected as shown below:

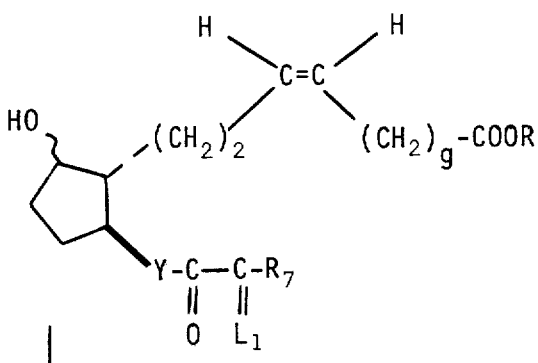   XLV

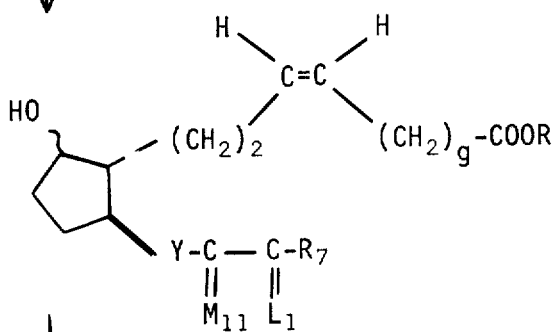   XLVI

UNITED STATES PATENT OFFICE
CERTIFICATE OF CORRECTION

Patent No. 3,987,072  Dated October 19, 1976

Inventor(s) Gordon L. Bundy and Norman A. Nelson

It is certified that error appears in the above-identified patent and that said Letters Patent are hereby corrected as shown below:

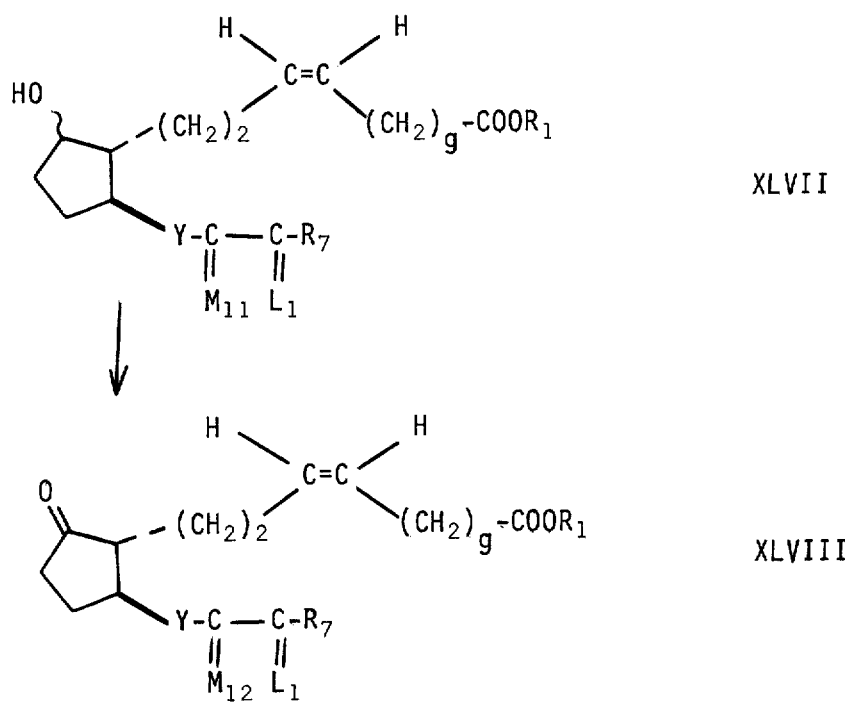

XLVII

XLVIII

UNITED STATES PATENT OFFICE
CERTIFICATE OF CORRECTION

Patent No. 3,987,072  Dated October 19, 1976

Inventor(s) Gordon L. Bundy and Norman A. Nelson

It is certified that error appears in the above-identified patent and that said Letters Patent are hereby corrected as shown below:

Chart D, appearing in columns 28 and 29, should read as follows:

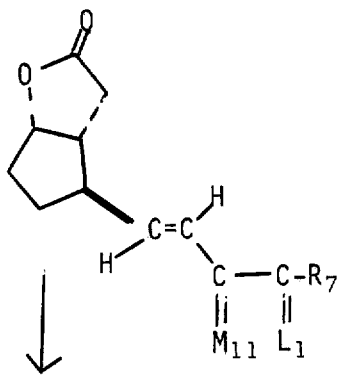

LI

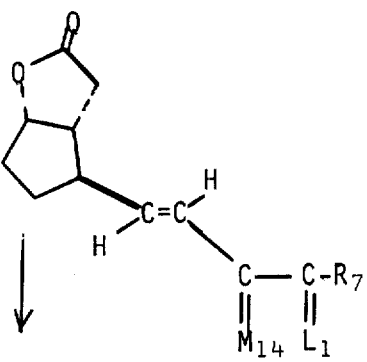

LII

UNITED STATES PATENT OFFICE
CERTIFICATE OF CORRECTION

Patent No. 3,987,072   Dated October 19, 1976

Inventor(s) Gordon L. Bundy and Norman A. Nelson

It is certified that error appears in the above-identified patent and that said Letters Patent are hereby corrected as shown below:

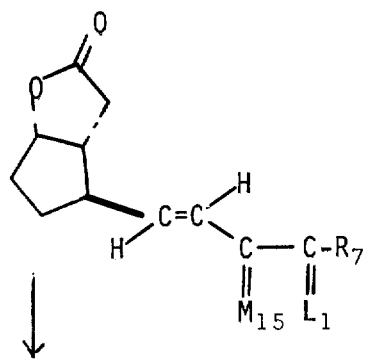

LIII

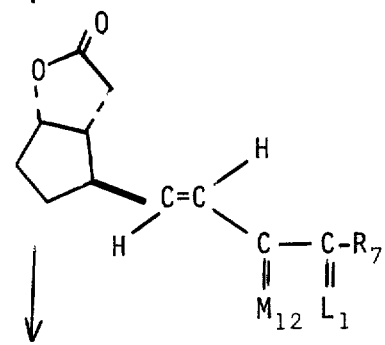

LIV

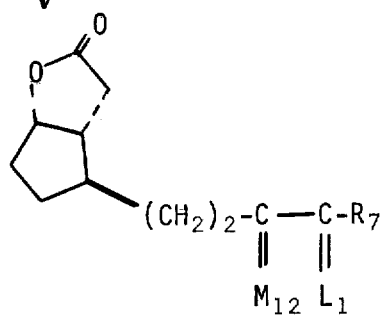

LV

UNITED STATES PATENT OFFICE
CERTIFICATE OF CORRECTION

Patent No. 3,987,072   Dated October 19, 1976

Inventor(s) Gordon L. Bundy and Norman A. Nelson

It is certified that error appears in the above-identified patent and that said Letters Patent are hereby corrected as shown below:

Column 33, line 66, "Br($C_6H_5$)$_3$P($CH_2$)$_5$COOH" should read -- Br($C_6H_5$)$_3$P($CH_2$)$_3$COOH --;

Column 34, line 42, "2-oxo-3-dimethyl" should read -- 2-oxo-3-methyl --; line 44, "cmpound" should read -- compound --;

Column 35, lines 20-22, " 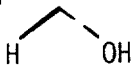 " should read 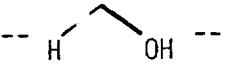 ;

Column 37, lines 59-61, " 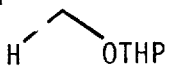 " should read 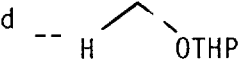 ;

Column 46, line 15, "at -20 C." should read -- at -20° C. --.

Signed and Sealed this

Seventh Day of March 1978

[SEAL]

Attest:

RUTH C. MASON
Attesting Officer

LUTRELLE F. PARKER
Acting Commissioner of Patents and Trademarks